United States Patent

Bisacchi et al.

Patent Number: 4,723,002
Date of Patent: Feb. 2, 1988

[54] 1-(SUBSTITUTED PHOSPHOROUS)-AZETIDINONE ANTIBACTERIALS

[75] Inventors: Gregory S. Bisacchi, Titusville; Glenn A. Jacobs, Princeton; William H. Koster, Pennington; Robert Zahler, Princeton, all of N.J.

[73] Assignee: E. R. Squibb & Sons, Inc.

[21] Appl. No.: 856,893

[22] Filed: Apr. 28, 1986

[51] Int. Cl.[4] .................. C07F 9/65; A61K 31/675
[52] U.S. Cl. ............................. 540/363; 540/357; 540/360; 540/364
[58] Field of Search ............... 540/357, 360, 363, 364

[56] References Cited

U.S. PATENT DOCUMENTS 4,478,749 10/1984 Koster et al. ................ 540/363

OTHER PUBLICATIONS

Abstract 646 from 1984 ICAAC Meeting; Mochida et al., "Antimicrobial Activities of 1-Carbacephem Compounds and Their Structure-Activity Relationships".

Primary Examiner—Mark L. Berch
Attorney, Agent, or Firm—Lawrence S. Levinson; Donald J. Barrack

[57] ABSTRACT

Antibacterial activity is exhibited by 2-azetidinones having an acylamino substituent in the 3-position and having an activating group in the 1-position of the formula

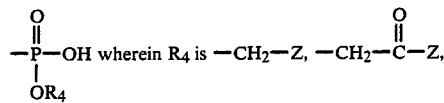

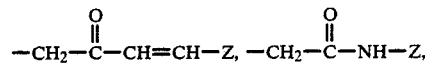

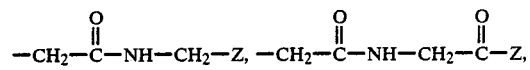

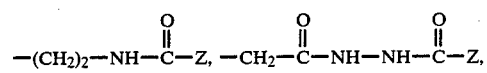

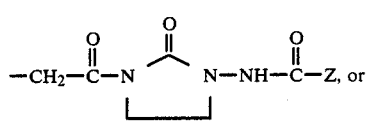

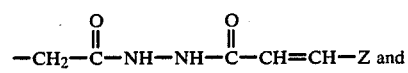

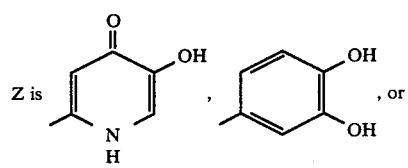

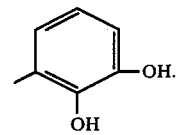

16 Claims, No Drawings

1-(SUBSTITUTED PHOSPHOROUS)-AZETIDINONE ANTIBACTERIALS

BACKGROUND OF THE INVENTION

U.S. Pat. No. 4,478,749, issued Oct. 23, 1984, describes antibiotics comprising a β-lactam nucleus having in the 3-position an acylamino substituent and in the 1-position an activating group of the formula

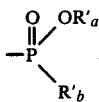

wherein $R'_a$ is hydrogen, alkyl, substituted alkyl, phenyl or substituted phenyl, and $R'_b$ is hydroxy, alkoxy, (substituted alkyl)oxy, phenyloxy, (substituted phenyl)oxy, alkyl, substituted alkyl, phenyl, substituted phenyl, heteroaryl, amino, substituted amino, alkylthio, (substituted alkyl)thio, phenylthio, (substituted phenyl)thio, 1-(ethoxycarbonyloxy)ethoxy, 1,3-dihydro-3-oxo-1-isobenofuranyloxy,

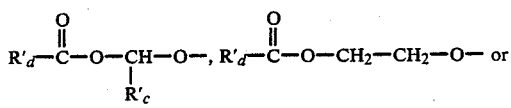

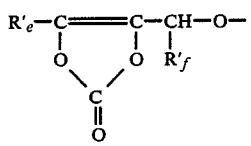

wherein $R'_c$ is hydrogen or alkyl, $R'_d$ is alkyl or phenyl, $R'_e$ is hydrogen, methyl or phenyl and $R'_f$ is hydrogen or together with $R'_e$ is $-(CH_2)_3-$ or $-(CH_2)_5-$.

BRIEF DESCRIPTION OF THE INVENTION

Compounds having the formula

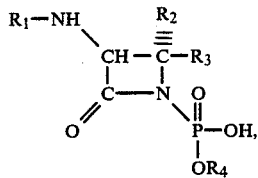

I and pharmaceutically acceptable salts thereof, exhibit antibacterial activity. In formula I, and throughout the specification, the symbols are as defined below.

$R_1$ is an acyl group derived from a carboxylic acid;

$R_2$ and $R_3$ are the same or different and each is hydrogen, alkyl, alkenyl, alkynyl, cycloalkyl, phenyl, substituted phenyl or a 4, 5, 6 or 7-membered heterocycle (hereinafter referred to as $R_x$), or one of $R_2$ and $R_3$ is hydrogen and the other is azido, halomethyl, dihalomethyl, trihalomethyl, alkoxycarbonyl, 2-phenylethenyl, 2-phenylethynyl, carboxyl, $-CH_2X_1$ [wherein $X_1$ is azido, amino ($-NH_2$), hydroxy, carboxyl, alkoxycarbonyl, alkanoylamino, phenylcarbonylamino, (substituted phenyl)carbonylamino, alkylsulfonyloxy, phenylsulfonyloxy, (substituted phenyl)sulfonyloxy, phenyl, substituted phenyl, cyano,

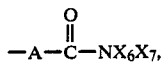

$-S-X_2$, or $-O-X_2$ (wherein A, $X_2$, $X_6$ and $X_7$ are as hereinafter defined)], $-S-X_2$ or $-O-X_2$ [wherein $X_2$ is alkyl, substituted alkyl, phenyl, substituted phenyl, phenylalkyl, (substituted phenyl)alkyl, alkanoyl, phenylalkanoyl, (substituted phenyl)carbonyl, or heteroarylcarbonyl],

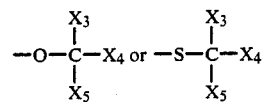

[wherein one of $X_3$ and $X_4$ is hydrogen and the other is hydrogen or alkyl, or $X_3$ and $X_4$ when taken together with the carbon atom to which they are attached form a cycloalkyl group; and $X_5$ is formyl, alkanoyl, phenylcarbonyl, (substituted phenyl)carbonyl, phenylalkylcarbonyl, (substituted phenyl)alkylcarbonyl, carboxyl, alkoxycarbonyl, aminocarbonyl

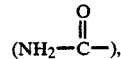

(substituted amino)carbonyl, or cyano ($-C\equiv N$)], or

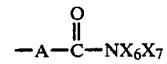

[wherein A is $-CH=CH-$, $-(CH_2)_m-$, $-(CH_2)_m-O-$, $-(CH_2)_m-NH-$, or $-CH_2-S-CH_2-$, m is 0, 1 or 2, and $X_6$ and $X_7$ are the same or different and each is hydrogen, alkyl, phenyl or substituted phenyl, or $X_6$ is hydrogen and $X_7$ is amino, substituted amino, alkanoylamino or alkoxy, or $X_6$ and $X_7$ when taken together with the nitrogen atom to which they are attached form a 4, 5, 6 or 7-membered heterocycle];

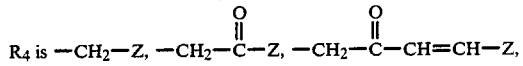

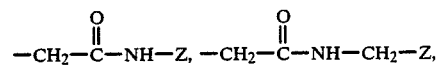

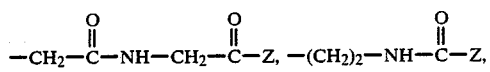

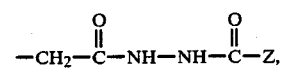

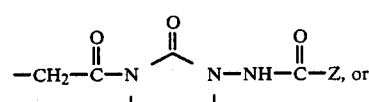

Z is 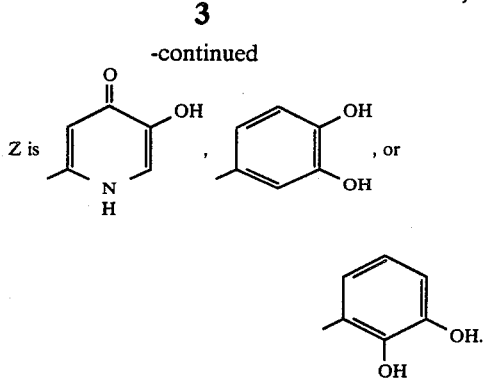

DETAILED DESCRIPTION OF THE INVENTION

Listed below are definitions of various terms used to describe the β-lactams of this invention. These definitions apply to the terms as they are used throughout the specification (unless they are otherwise limited in specific instances) either individually or as part of a larger group.

The terms "alkyl" and "alkoxy" refer to both straight and branched chain groups. Those groups having 1 to 10 carbon atoms are preferred.

The terms "cycloalkyl" and "cycloalkenyl" refer to cycloalkyl and cycloalkenyl groups having 3, 4, 5, 6 or 7 carbon atoms.

The term "substituted alkyl" refers to alkyl groups substituted with one or more (preferably 1, 2 or 3) azido, amino ($-NH_2$), halogen, hydroxy, carboxy, cyano, alkoxycarboonyl, aminocarbonyl, alkanoyloxy, alkoxy, phenyloxy, (substituted phenyl)oxy, mercapto, alkylthio, phenylthio, (substituted phenyl)thio, alkylsulfinyl, or alkylsulfonyl groups.

The terms "alkanoyl", "alkenyl", and "alkynyl" refer to both straight and branched chain groups. Those groups having 2 to 10 carbon atoms are preferred.

The terms "halogen" and "halo" refer to fluorine, chlorine, bromine and iodine.

The term "substituted phenyl" refers to a phenyl group substituted with 1, 2 or 3 amino ($-NH_2$), halogen, hydroxyl, trifluoromethyl, alkyl (of 1 to 4 carbon atoms), alkoxy (of 1 to 4 carbon atoms), alkanoyloxy, aminocarbonyl, or carboxy groups.

The expression "a 4, 5, 6 or 7-membered heterocycle" (referred to as "$R_x$") refers to substituted and unsubstituted, aromatic and non-aromatic groups containing one or more (preferably 1, 2 or 3) nitrogen, oxygen or sulfur atoms. Exemplary substituents are oxo (=O), halogen, hydroxy, nitro, amino, cyano, trifluoromethyl, alkyl of 1 to 4 carbons, alkoxy of 1 to 4 carbons, alkylsulfonyl, phenyl, substituted phenyl, 2-furfurylideneamino (  ), benzylideneamino and substituted alkyl groups (wherein the alkyl group has 1 to 4 carbons). One type of "4, 5, 6 or 7-membered heterocycle" is the "heteroaryl" group. The term "heteroaryl" refers to those 4, 5, 6 or 7-membered heterocycles which are aromatic. Exemplary heteroaryl groups are substituted and unsubstituted pyridinyl, furanyl, pyrrolyl, thienyl, 1,2,3-triazolyl, 1,2,4-triazolyl, imidazolyl, thiazolyl, thiadiazolyl, pyrimidinyl, oxazolyl, triazinyl, and tetrazolyl. Exemplary nonaromatic heterocycles (i.e., fully or partially saturated heterocyclic groups) are substituted and unsubstituted azetidinyl, oxetanyl, thietanyl, piperidinyl, piperazinyl, imidazolidinyl, oxazolidinyl, pyrrolidinyl, tetrahydropyrimidinyl, dihydrothiazolyl and hexahydroazepinyl. Exemplary of the substituted 4, 5, 6 or 7-membered heterocycles are 1-alkyl-3-azetidinyl, 2-oxo-1-imidazolidinyl, 3-alkylsulfonyl-2-oxo-1-imidazolidinyl, 3-benzylideneamino-2-oxo-1-imidazolidinyl, 3-alkyl-2-oxo-1-imidazolidinyl, 3-phenyl (or substituted phenyl)-2-oxo-1-imidazolidinyl, 3-benzyl-2-oxo-1-imidazolidinyl, 3-(2-aminoethyl)-2-oxo-1-imidazolidinyl, 3-amino-2-oxo-1-imidazolidinyl, 3-[(alkoxycarbonyl)amino]-2-oxo-1-imidazolidinyl, 3-[2-[(alkoxycarbonyl)amino]ethyl]-2-oxo-1-imidazolidinyl, 2-oxo-1-pyrrolidinyl, 2-oxo-3-oxazolidinyl, 4-hydroxy-6-methyl-2-pyrimidinyl, 2-oxo-1-hexahydroazepinyl, 2-oxo-3-pyrrolidinyl, 2-oxo-3-tetrahydrofuranyl, 2,3-dioxo-1-piperazinyl, 2,5-dioxo-1-piperazinyl, 4-alkyl-2,3-dioxo-1-piperazinyl, and 4-phenyl-2,3-dioxo-1-piperazinyl.

The term "substituted amino" refers to a group having the formula $-NX_8X_9$ wherein $X_8$ is hydrogen, alkyl, phenyl, substituted phenyl, phenylalkyl or (substituted phenyl)alkyl, and $X_9$ is alkyl, phenyl, substituted phenyl, phenylalkyl, (substituted phenyl)alkyl, hydroxy, cyano, alkoxy, phenylalkoxy, or amino ($-NH_2$).

The term "acyl" refers to all organic radicals derived from an organic acid (i.e., a carboxylic acid) by removal of the hydroxyl group. Certain acyl groups are, of course, preferred but this preference should not be viewed as a limitation of the scope of this invention. Exemplary acyl groups are those acyl groups which have been used in the past to acylate β-lactam antibiotics including 6-aminopenicillanic acid and derivatives and 7-aminocephalosporanic acid and derivatives; see, for example, *Cephalosporins and Penicillins*, edited by Flynn, Academic Press (1972), German Offenlegungsschrift No. 2,716,677, published Oct. 10, 1978, Belgian Pat. No. 867,994, published Dec. 11, 1978, U.S. Pat. No. 4,152,432, issued May 1, 1979, U.S. Pat. No. 3,971,778, issued July 27, 1976, U.S. Pat. No. 4,172,199, issued Oct. 23, 1979, and British Pat. No. 1,348,894, published Mar. 27, 1974. The portions of these references describing various acyl groups are incorporated herein by reference. The following list of acyl groups is presented to further exemplify the term "acyl"; it should not be regarded as limiting that term. Exemplary acyl groups are:

(a) Aliphatic groups having the formula

wherein $R_a$ is alkyl; cycloalkyl; alkoxy; alkenyl; cycloalkenyl; cyclohexadienyl; or alkyl or alkenyl substituted with one or more halogen, cyano, nitro, amino, mercapto, alkylthio, or cyanomethylthio groups.

(b) Carbocyclic aromatic groups having the formula

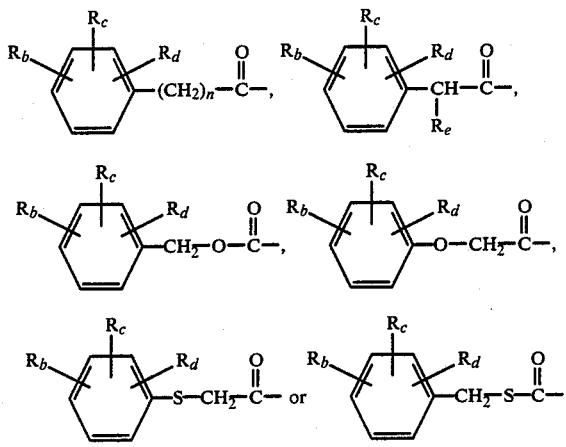

wherein n is 0, 1, 2 or 3; $R_b$, $R_c$, and $R_d$ each is independently hydrogen, halogen, hydroxyl, nitro, amino, cyano, trifluoromethyl, alkyl of 1 to 4 carbon atoms, alkoxy of 1 to 4 carbon atoms or aminomethyl; and $R_e$ is amino, hydroxyl, a carboxyl salt, protected carboxyl, formyloxy, a sulfo salt, a sulfoamino salt, azido, halogen, hydrazino, alkylhydrazino, phenylhydrazino, or [(alkylthio)thioxomethyl]thio.

Preferred carbocyclic aromatic acyl groups include those having the formula

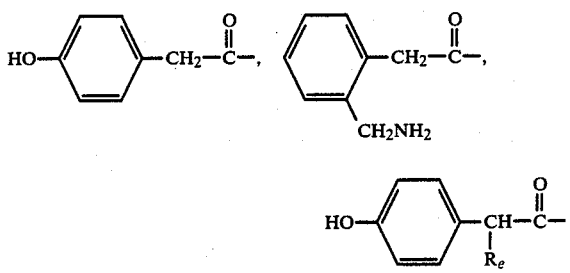

($R_e$ is preferably a carboxyl salt or sulfo salt) and

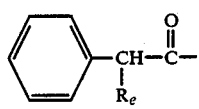

($R_e$ is preferably a carboxyl salt or sulfo salt).

(c) Heteroaromatic groups having the formula

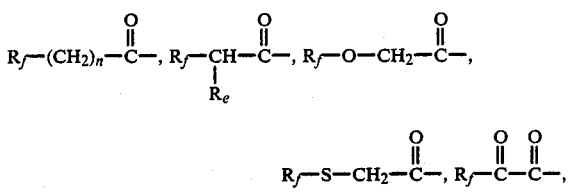

wherein n is 0, 1, 2 or 3; $R_e$ is as defined above; and $R_f$ is a substituted or unsubstituted 5-, 6- or 7-membered heterocyclic ring containing 1, 2, 3 or 4 (preferably 1 or 2) nitrogen, oxygen and sulfur atoms. Exemplary heterocyclic rings are thienyl, furyl, pyrrolyl, pyridinyl, pyrazolyl, pyrazinyl, thiazolyl, pyrimidinyl, thiadiazolyl and tetrazolyl. Exemplary substituents are halogen, hydroxyl, nitro, amino, protected amino, cyano, trifluoromethyl, alkyl of 1 to 4 carbon atoms, alkoxy of 1 to 4 carbon atoms, or

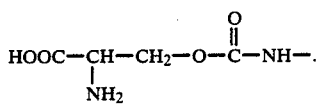

Preferred heteroaromatic acyl groups include those groups of the above formulas wherein $R_f$ is 2-amino-4-thiazolyl, 2-amino-5-halo-4-thiazolyl, 4-aminopyrimidin-2-yl, 5-amino-1,2,4-thiadiazol-3-yl, 2-thienyl, 2-furanyl, or 6-aminopyridin-2-yl.

(d) [[(4-Substituted-2,3-dioxo-1-piperazinyl)carbonyl]amino]arylacetyl groups having the formula

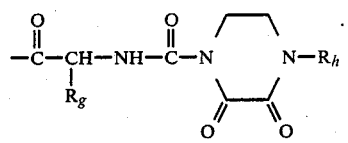

wherein $R_g$ is an aromatic group (including carbocyclic aromatics such as those of the formula

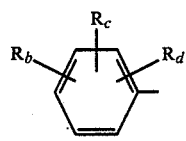

and heteroaromatics as included within the definition of $R_f$); and $R_h$ is alkyl, substituted alkyl (wherein the alkyl group is substituted with one or more halogen, cyano, nitro, amino or mercapto groups), arylmethyleneamino (i.e., $-N=CH-R_g$ wherein $R_g$ is as defined above), arylcarbonylamino (i.e.,

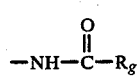

wherein $R_g$ is as defined above) or alkylcarbonylamino.

Preferred [[(4-substituted-2,3-dioxo-1-piperazinyl)carbonyl]amino]arylacetyl groups include those wherein $R_h$ is ethyl, phenylmethyleneamino or 2-furylmethyleneamino.

(e) (Substituted oximino)arylacetyl groups having the formula

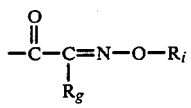

wherein $R_g$ is as defined above and $R_i$ is hydrogen, alkyl, cycloalkyl,

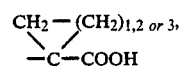

2-pyrrazolylmethyl, (2-oxo-3-pyrrolidinyl)methyl, alkylaminocarbonyl, arylaminocarbonyl (i.e.,

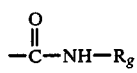

wherein $R_g$ is as defined above) or substituted alkyl (wherein the alkyl group is substituted with one or more halogen, cyano, nitro, amino, mercapto, alkylthio, aromatic group (as defined by $R_g$), carboxyl (including salts thereof), amido, alkoxycarbonyl, phenylmethoxycarbonyl, diphenylmethoxycarbonyl, hydroxyalkoxyphosphinyl, dihydroxyphosphinyl, hydroxy(phenylmethoxy)phosphinyl, dialkoxyphosphinyl or tetrazolyl substituents).

Preferred (substituted oxyimino)arylacetyl groups include those wherein $R_g$ is 2-amino-4-thiazolyl. Also preferred are those groups wherein $R_1$ is methyl, ethyl, carboxymethyl, 1-carboxy-1-methylethyl, 2,2,2-trifluoroethyl or 1-carboxycyclopropyl.

(f) (Acylamino)arylacetyl groups having the formula

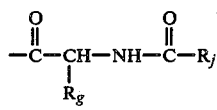

wherein $R_g$ is as defined above and $R_j$ is

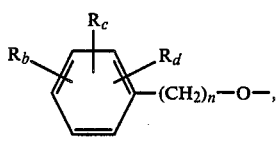

amino, alkylamino, (cyanoalkyl)amino, amido, alkylamido, (cyanoalkyl)amido,

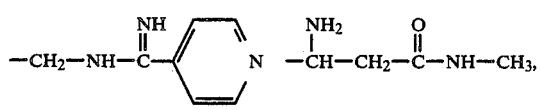

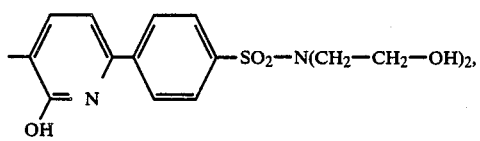

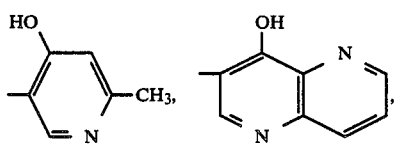

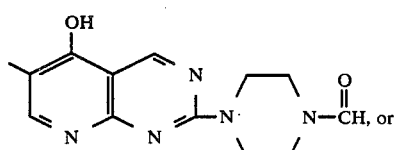

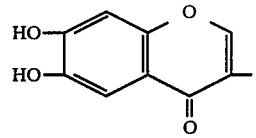

Preferred (acylamino)arylacetyl groups of the above formula include those groups wherein $R_j$ is amino or amido. Also preferred are those groups wherein $R_g$ is phenyl or 2-thienyl.

(g) [[[3-Substituted-2-oxo-1-imidazolidinyl]carbonyl]amino]arylacetyl groups having the formula

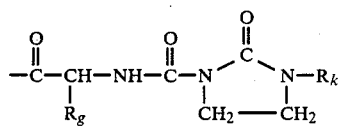

wherein $R_g$ is as defined above and $R_k$ is hydrogen, alkylsulfonyl, arylmethyleneamino (i.e., $-N=CH-R_g$ wherein $R_g$ is as defined above,

(wherein $R_m$ is hydrogen, alkyl or halogen substituted alkyl), aromatic group (as defined by $R_g$ above), alkyl or substituted alkyl (wherein the alkyl group is substituted with one or more halogen, cyano, nitro, amino or mercapto groups).

Preferred [[3-substituted-2-oxo-1-imidazolidinyl]carbonyl]amino]arylacetyl groups of the above formula include those wherein $R_g$ is phenyl or 2-thienyl. Also preferred are those groups wherein $R_k$ is hydrogen, methylsulfonyl, phenylmethyleneamino or 2-furylmethyleneamino.

The compounds of this invention form basic salts with various inorganic and organic bases which are also within the scope of this invention. Such salts include ammonium salts, alkali metal salts, alkaline earth metal salts, salts with organic bases, e.g., dicyclohexylamine, benzathine, N-methyl-D-glucamine, hydrabramine and the like. The pharmaceutically acceptable salts are preferred, although other salts are also useful, e.g., in isolating or purifying the product.

Some of the compounds of this invention may be crystallized or recrystallized from solvents containing water. In these cases, water of hydration may be formed. This invention contemplates stoichiometric hydrates as well as compounds containing variable amounts of water that may be produced by processes such as lyophilization.

The β-lactams of formula I contain at least one chiral center—the carbon atom in the 3-position of the β-lactam nucleus to which the acylamino substituent ("$R_1$—NH—") is attached. This invention is directed to those β-lactams which have been described above, wherein the stereochemistry at the chiral center in the 3-position of the β-lactam nucleus is the same as the configuration at the carbon atom in the 6-position of naturally occurring penicillins (e.g., penicillin G). Also included within the scope of this invention are racemic mixtures which contain the above-described β-lactams.

The β-lactams of formula I, and pharmaceutically acceptable salts thereof, have activity against gram-positive and gram-negative organisms. The compounds of this invention can be used as agents to combat bacterial infections (including urinary tract infections and respiratory infections) in mammalian species, such as domesticated animals (e.g., dogs, cats, cows, horses, and the like) and humans.

For combating bacterial infections in mammals, a compound of this invention can be administered to a mammal in need thereof in an amount of about 1.4 mg/kg/day to about 350 mg/kg/day, preferably about 14 mg/kg/day to about 100 mg/kg/day. All modes of administration which have been used in the past to deliver penicillins and cephalosporins to the site of the infection are also contemplated for use with β-lactams of this invention. Such methods of administration include oral, intravenous, intramuscular, and as a suppository.

The β-lactams of formula I can be prepared from a compound having the formula

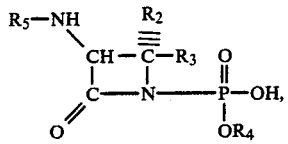
II or a salt thereof. In formula II, and throughout the specification, the symbol "$R_5$" refers to an amino protecting group. These groups are well known in the field of β-lactam chemistry. Benzyloxycarbonyl, trityl, and t-butoxycarbonyl are exemplary protecting groups. In formula II, it is to be understood that the dihydroxyphenyl or 5-hydroxy-4-pyridone moiety of the $R_4$ group is optionally protected. Protected forms of the $R_4$ group, or of any reactant described herein which contains a 2,3-dihydroxyphenyl, 3,4-dihydroxyphenyl or 5-hydroxy-4-pyridone moiety, includes those forms wherein the hydroxyl groups are protected, those forms wherein the hydroxyl group and the ring nitrogen are protected and those forms wherein both pyridone oxygens are protected. Exemplary protecting groups are trialkylsilyl (e.g., trimethylsilyl), benzyl and acyl (e.g., acetyl).

Deprotection of a compound of formula II using conventional techniques yields the corresponding key intermediate having the formula

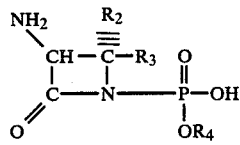
III or a salt thereof, wherein the optionally protected $R_4$ group is now deprotected. Deprotection of a compound of formula II can proceed, if required, in a sequential manner (such as deprotection of $R_4$ followed by removal of $R_5$), or it can proceed by simultaneous deprotection of $R_4$ (if required) and removal of $R_5$. The particular deprotection reaction (or reactions) will, of course, depend on the protecting groups present. If, for example, $R_5$ is t-butoxycarbonyl and the protecting group(s) of $R_4$ are acyl, deprotection can be accomplished by sequential treatment of a compound of formula II with e.g., ammonium acetate in water (to remove the acyl protecting groups of $R_4$) followed by an acid, e.g. formic acid or trifluoroacetic acid, (to remove the t-butoxycarbonyl group, $R_5$). If, for example, $R_5$ is benzyloxycarbonyl and the protecting group(s) of $R_4$ are benzyl, full deprotection can be accomplished by catalytic hydrogenation of a compound of formula II.

Well known acylation techniques can be used to convert an intermediate of formula III to a corresponding product of formula I. Exemplary techniques include reaction of a compound of formula III with a carboxylic acid ($R_1$—OH), or corresponding carboxylic acid halide or carboxylic acid anhydride. The reaction with a carboxylic acid proceeds most readily in the presence of a carbodiimide such as dicyclohexylcarbodiimide and a substance capable of forming an active ester in situ such as N-hydroxybenzotriazole. Alternatively, this active ester can be isolated in pure form (rather than being generated in situ) and then used to convert a compound of formula III to a corresponding product of formula I. In those instances where the acyl group ($R_1$) contains reactive functionality (such as amino or carboxyl groups) it may be necessary to first protect those functional groups, then carry out the acylation reaction, and finally deprotect the resulting product.

Compounds of formula II wherein $R_4$ is

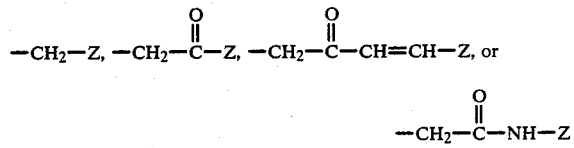

(and Z is optionally protected) can be prepared by reacting a compound having the formula

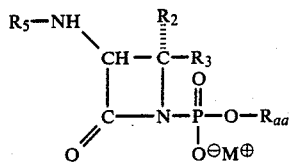
IV wherein $R_{aa}$ is ethyl or methyl and $M^\oplus$ is a tetraalkylammonium ion, with a suitably protected derivative of a compound of the formula

V

VI

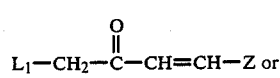
VII

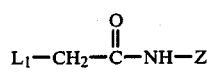
VIII wherein $L_1$ is a leaving group (e.g., a halide such as chloride, bromide or iodide; a mesylate or a tosylate). A general description of the above-described type of reaction can be found in U.S. Pat. No. 4,478,749, issued Oct. 23, 1984 and in J. Amer. Chem. Soc., 105, 3743 (1983). When $L_1$ is a non-halide leaving group such as mesylate or tosylate, a tetraalkylammonium halide must also be present in the reaction mixture. The resulting product of the above reactions is a tetraalkylammonium salt of a compound of formula II, which can be converted to other salts using conventional methodology (e.g., ion exchange chromatography).

Suitably protected compounds of formula V can be prepared by reacting suitably protected compounds having the formula

HO—CH₂—Z    IX with any of various reagents known in the art which convert a hydroxyl group to an appropriate leaving group L₁ (e.g., thionyl chloride for conversion to the chloride or mesyl chloride/triethylamine for conversion to the mesylate).

Suitably protected compounds of formula VI wherein L₁ is chloride, bromide or iodide can be prepared from an activated suitably protected derivative of an acid of the formula

HO₂C—Z    X by reaction with diazomethane followed by reaction with hydrochloric acid to afford the suitably protected compound of formula VI where L₁ is chloride. The chloride can then be converted to the corresponding bromide by reaction with, for example, an excess of potassium bromide in dimethylformamide, and to the corresponding iodide by reaction with, for example, sodium iodide in refluxing acetone. An activated derivative of the acid of formula X (suitably protected) can be a mixed anhydride (prepared from a reagent such as isobutyl chloroformate) or the corresponding acid chloride (prepared from a reagent such as phosphorous pentachloride).

Suitably protected compounds of formula VII where L₁ is chloride, bromide, or iodide can be prepared starting from the alcohol of formula IX (suitably protected) by oxidation to the corresponding aldehyde (with a reagent such as manganese dioxide), reacting the aldehyde with a carboxyl-protected derivative having the formula

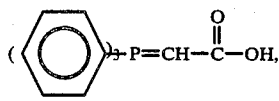    XII and deprotection of the carboxyl group to yield

HO₂CCH=CH—Z    XIII wherein Z is suitably protected. An activated, suitably protected compound of formula XIII can then be reacted with diazomethane followed by hydrochloric acid to afford the suitably protected compound of formula VII wherein L₁ is chloride, which can be converted to the corresponding bromide or iodide by the methods described above for the conversion of the compound of formula VI where L₁ is chloride. Compound XIII can be activated in the manner described above for the activation of the compound of formula X.

Suitably protected compounds of formula VIII wherein L₁ is halide such as chloride, bromide or iodide can be prepared by reacting a suitably protected compound having the formula

H₂N—Z    XIV with a haloacetyl halide (such as chloroacetyl chloride for conversion to the chloride). A compound of formula XIV wherein Z is a suitably protected 5-hydroxy-4-pyridone can be prepared starting from the acid of formula X wherein Z is 5-hydroxy-4-pyridone (suitably protected) by the following sequence of reactions: esterification with ethanol-hydrochloric acid to afford the corresponding ethyl ester, treatment of the ethyl ester with hydrazine to afford the corresponding hydrazide, reaction of the hydrazide with nitrous acid to yield the corresponding carbonyl azide which can then be heated in the presence of an alcohol (such as methyl, ethyl, t-butyl, benzyl, or β-trimethylsilylethyl alcohol) to give the corresponding urethane of formula XV

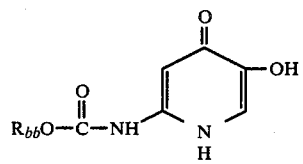    XV wherein the 5-hydroxy-4-pyridone moiety is suitably protected and $R_{bb}$ is methyl, ethyl, t-butyl, benzyl, or β-trimethylsilylethyl. Alternatively, a compound of formula XV (suitably protected) can be prepared from a compound of formula XIV (where Z is a suitably protected 3-hydroxy-4-pyridone) by reaction with diphenylphosphoryl azide in the presence of an alcohol such as t-butyl alcohol to give directly the urethane of formula XV wherein the 5-hydroxy-4-pyridone moiety is suitably protected and $R_{bb}$ is t-butyl. Finally, removal of the exocyclic amino protecting group

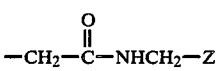

affords a compound of formula XIV (wherein the 5-hydroxy-4-pyridone moiety is suitably protected).

Compounds of formula II wherein R₄ is

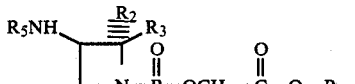

(and Z is optionally protected) can be prepared by reacting a sodium, potassium or tetraalkylammonium salt of a compound having the formula

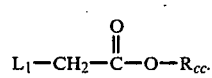    XVI (wherein $R_{cc}$ is an alkyl or substituted alkyl group, e.g., methyl, ethyl or benzyl) with a suitably protected compound having the formula

H₂N—CH₂—Z.    XVII

A compound of formula XVI can be prepared by reacting a compound of formula IV with a compound having the formula L₁—CH₂—C(=O)—O—R_{cc}.    XVIII This reaction can be carried out in a manner similar to that described above for the reaction of compounds of formulas V to VIII with a compound of formula IV. The resultant tetraalkylammonium salt can be readily converted to other salts.

A compound of formula XVII (suitably protected) can be prepared by reacting a compound of formula V (suitably protected) with sodium azide to yield $$N_3-CH_2-Z \qquad \text{XIX}$$

(suitably protected) followed by reduction of the azido moiety with hydrogen in the presence of a catalyst such as platinum oxide.

Compounds of formula II wherein $R_4$ is $$-CH_2\overset{O}{\overset{\|}{C}}-NHCH_2-\overset{O}{\overset{\|}{C}}-Z$$

(and Z is optionally protected) can be prepared by reacting an activated form of a compound having the formula <chemical structure XX>
R_5NH, R_2, R_3
O=...−N−P(=O)(OCH_3)−OCH_2CO_2H with a suitably protected compound having the formula $$H_2NCH_2-\overset{O}{\overset{\|}{C}}-Z \qquad \text{XXI}$$

to yield a suitably protected compound having the formula

<chemical structure XXII>
R_5NH, R_2, R_3
O=...−N−P(=O)(OCH_3)−OCH_2−C(=O)−NH−CH_2−C(=O)−Z.

An activated derivative of a compound of formula XX can be a mixed anhydride (prepared from reagents such as isobutylchloroformate or diphenylchlorophosphate) or the corresponding acid chloride (prepared from a reagent such as phosphorous pentachloride, oxalyl chloride, triphenylphosphine/carbon tetrachloride or thionyl chloride). A compound of formula XX can be prepared by treating a tetrabutylammonium salt of compound of formula XVI (wherein $R_{cc}$ is a protecting group which can be selectively removed in the presence of $R_5$) with dimethylsulfate followed by removal of $R_{cc}$.

A suitably protected compound of formula XXI (or salts thereof with strong acids) can be prepared by reaction of a suitably protected compound of formula VI with sodium azide to yield $$N_3-CH_2-\overset{O}{\overset{\|}{C}}-Z, \qquad \text{XXIII}$$

followed by reduction with hydrogen in the presence of a strong acid such as hydrochloric or tosic acid and a catalyst such as platinum oxide.

Treatment of a compound of formula XXII with a nucleophile such as thiourea or a tetraalkylammonium halide yields the S-methylthiuronium or tetraalkylammonium salt of the corresponding compound of formula II. Conversion to other salts is readily accomplished using standard methodology.

Compounds of formula II wherein $R_4$ is $$-(CH_2)_2-NH-\overset{O}{\overset{\|}{C}}-Z,\ -CH_2-\overset{O}{\overset{\|}{C}}-NH-NH-\overset{O}{\overset{\|}{C}}-Z,\ \text{or}$$

$$-CH_2-\overset{O}{\overset{\|}{C}}-N\underset{\underset{O}{\overset{\|}{C}}}{\overbrace{\phantom{XXXX}}}N-NH\overset{O}{\overset{\|}{C}}-Z$$

(wherein Z is optionally protected) can be prepared by reacting an activated, suitably protected form of a compound of formula X with a compound of the formula <chemical structure XXIV>
R_5NH, R_2, R_3
O=...−N−P(=O)(OH)−OCH_2CH_2NH_2, <chemical structure XXV>
R_5NH, R_2, R_3
O=...−N−P(=O)(OH)−OCH_2C(=O)NHNH_2 or <chemical structure XXVI>
R_5NH, R_2, R_3
O=...−N−P(=O)(OH)−OCH_2−C(=O)−N(ring with C=O)N−NH_2, or a suitable salt thereof.

The acid of formula X can be activated with dicyclohexylcarbodiimide, or a combination of dicyclohexylcarbodiimide and N-hydroxybenzotriazole. Alternatively, an activated derivative of formula X can be the corresponding acid chloride (prepared with a reagent such as thionyl chloride or phosphorous pentachloride) or a mixed anhydride (prepared with a reagent such as diphenylphosphoryl chloride, pivaloyl chloride or isobutyl chloroformate).

A compound of formula XXIV can be prepared by reacting a compound of formula XXVII with N-tritylaziridine and subsequent removal of the trityl protecting group.

<chemical structure XXVII>
R_5NH, R_2, R_3
O=...−N−P(=O)(OH)−OH

A salt of a compound of formula XXV can be prepared by reacting a sodium or potassium salt of a compound of formula XVI (wherein $R_{cc}$ is benzyl) with hydrazine.

A compound of formula XXVI can be prepared by reacting a compound of formula IV with a compound having the formula

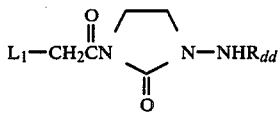
XXVIII where $L_1$ is a chloride, bromide or iodide and $R_{dd}$ is an amine protecting group which can be removed selectively in the presence of $R_5$. For example, when $R_5$ is benzyloxycarbonyl, $R_{dd}$ can be t-butoxycarbonyl. This reaction can be carried out in a manner similar to that described above for the reaction of compounds of formulas V to VIII with a compound of formula IV. The resultant tetraalkylammonium salt form of formula II can be readily converted to other salt forms.

A compound of formula XXVIII can be prepared by reaction of a compound having the formula

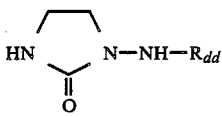
XXIX with an appropriate haloacetyl halide.

Compounds of formula II wherein $R_4$ is

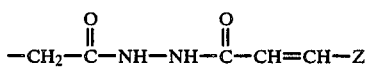

(where Z is optionally protected) can be prepared by reacting an activated, suitably protected form of a compound of formula XIII with a compound of formula XXV or a suitable salt thereof. The acid of formula XIII can be activated by any of the methods described above for the activation of the acid of formula X.

The following examples are specific embodiments of this invention.

EXAMPLE 1

[2S-[2α,3β(Z)]]-2-[[[1-(2-Amino-4-thiazolyl)-2-[[1-[[2-[[(1,4-dihydro-5-hydroxy-4-oxo-2-pyridinyl)-2-oxoethoxy]hydroxyphosphinyl]-2-methyl-4-oxo-3-azetidinyl]amino]-2-oxoethylidene]amino]-oxy]-2-methylpropanoic acid (A) 2-(Hydroxymethyl)-5-(phenylmethoxy)-4H-pyran-4-one 69 g (3 mmol) of sodium were dissolved in 5 l of methanol. Subsequently 425.3 g (3 mol) of 5-hydroxy-2-(hydroxymethyl)-4H-pyran-4-one was added and stirred at 30° C. until a clear solution was obtained. 595 g (3.5 mol) of benzyl bromide was then added and stirred for 1 hour under reflux. The warm, dark colored solution was poured into 15 l of ice water. The product crystallized immediately. The crystals were collected and washed first with 8 l of water and then twice with 2.5 l of ether. The product was left to stand overnight and finally dried at 50° C. for 16 hours. Yield: 646 g.

(B) 4-Oxo-5-(phenylmethoxy)-4H-pyran-2-carboxylic acid 232 g (1 mol) of 2-(hydroxymethyl)-5-(phenylmethoxy)-4H-pyran-4-one was put into a 10 l stirring flask containing 6.6 l of acetone and 400 ml of water. The clear solution was cooled to +5° C. by means of an ice bath. While maintaining the temperature at +5° C. to 10° C., 640 ml of Jones reagent (202 g $CrO_3$, 600 ml water, 174 ml $H_2SO_4$) was added dropwise over a period of 1 hour. Stirring was continued for 2 hours without cooling. The reaction mixture was filtered through a glass frit and the dark green residue washed with 500 ml of acetone. The filtrate was then evaporated until all of the acetone was removed. To the aqueous, partly crystalline product was added 1.2 l of methanol, and this mixture was then heated to its boiling point. The resulting clear dark green solution was placed in an ice bath and the product allowed to crystallize. The crystalline product was filtered and washed with 500 ml of a cold solvent mixture consisting of 250 ml of methanol +250 ml of water and finally dried. Yield: 195 g. From the mother liquor, a further 5% of the product could be isolated.

(C) 1,4-Dihydro-4-oxo-5-(phenylmethoxy)-2-pryidinecarboxylic acid 300 g (1.22 mol) of 4-oxo-5-(phenylmethoxy)-4H-pyran-2-carboxylic acid was put into a flask and 5 l of 33% ammonium hydroxide was carefully added with stirring. The reaction mixture was then stirred under reflux. After 3 hours, one additional liter of 33% ammonium hydroxide was added slowly. Stirring was continued for further 2 hours under reflux. The reaction solution was then evaporated until the product crystallized. The product was transferred back into the reaction flask and water added until a clear solution was obtained (approximately 5 l, pH 6.38). This solution was stirred vigorously while concentrated hydrochloric acid was added dropwise until a pH of 3 was obtained. The precipitated white product was removed by filtration, thoroughly washed with water and dried. Yield: 273 g.

(D) 4,5-Bis(phenylmethoxy)-2-pyridinecarboxylic acid, phenylmethyl ester

N,N-Diisopropylethylamine (15.66 ml, 90 mmole) was added to a stirred suspension of 1,4-dihydro-4-oxo-5-(phenylmethoxy)-2-pyridinecarboxylic acid (10.05 g, 41 mmole) in 90 ml of dimethylformamide containing 9.77 ml (90 mmole) of benzyl bromide. The solid went into solution after a few seconds and the mixture was stirred overnight. Volatiles were removed in vacuo affording a solid residue which was partitioned between water and ethyl acetate. The organic phase was separated and the aqueous phase was extracted three times with ethyl acetate. The organics were combined and dried over sodium sulfate. The drying agent was separated and the solvent was removed in vacuo to afford a solid residue. The crude product mixture was chromatographed on a column of silica gel eluting with chloroform-methanol. Combination and concentration of appropriate fractions afforded 3.384 g of the title compound as a white solid.

(E) 4,5-Bis(phenylmethoxy)-2-pyridinecarboxylic acid

To a solution of 4,5-bis(phenylmethoxy)-2-pyridinecarboxylic acid, phenylmethyl ester (1.60 g, 3.76 mmole) in 15 ml of tetrahydrofuran and 2.2 ml of water was added 4 ml of 1N aqueous potassium hydroxide. The mixture was stirred at room temperature overnight. Water (15 ml) was added and 1N hydrochloric acid was added slowly with stirring while monitoring the pH. The pH of the mixture fell steadily to ca. 6.2 whereupon a large amount of solid began to separate and no further decrease in the pH was noted. Continued addition of hydrochloric acid eventually effected a sudden drop in pH to 3.2 and the addition was stopped. The solid was filtered and washed well with water, then ether, and dried in vacuo to afford 1.197 g of the title compound as a white waxy solid.

(F) 2-(Chloroacetyl)-4,5-bis(phenylmethoxy)pyridine

A suspension of 4,5-bis(phenylmethoxy)-2-pyridinecarboxylic acid (0.850 g, 2.54 mmole) in 12 ml of dry dimethylformamide was evacuated (0.07 mm of Hg) for about three minutes. N-Methylmorpholine (307 μl, 282 mg, 2.79 mmole) was added and the mixture was warmed at ca. 70° C. for a few minutes. One ml of dimethylformamide was added and the mixture again heated briefly to effect complete dissolution of 4,5-bis(-phenylmethoxy)-2-pyridinecarboxylic acid. The solution was cooled to −20° C. and isobutylchloroformate (362 μl, 381 mg, 2.79 mmole) was added. A precipitate formed. The mixture was allowed to warm to room temperature and most of the dimethylformamide was removed in vacuo (bulb-to-bulb; room temperature pot, −78° C. receiver). Dry tetrahydrofuran (15 ml) was added to the residue and a solution of diazomethane prepared as described below was added rapidly with stirring at room temperature. Moderate evolution of gas was observed.

Diazomethane was generated immediately prior to the operation described above, as follows. N-Methyl-N′-nitro-N-nitrosoguanidine (2.367 g, 16.1 mmole) was added in portions (over ca. three minutes) to a stirred ice-cold mixture of ether (15 ml) and 40% aqueous potassium hydroxide (8 ml). The mixture was stirred for 45 minutes at 0° C. (dry ice condenser over flask), decanted over solid potassium hydroxide and stored at 0° C. until ready for use, and finally decanted into a clean dry flask for use.

The reaction mixture was stirred for two hours at room temperature. Anhydrous hydrochloric acid dissolved in dry dioxane (10.3 ml of a 1.48M solution, 15.2 mmole) was added over three minutes with stirring. A thick precipitate formed which made stirring difficult. Sufficient glacial acetic acid (ca. 60 ml) was added to effect complete dissolution of the solid. Ether (ca. 100 ml) and ethyl acetate (ca. 200 ml) were added. With cooling in an ice bath, aqueous and solid sodium carbonate were then carefully added with stirring while monitoring pH. The pH of the aqueous phase was taken to 8.35. The organic phase, checked with moist pH paper was non-acidic. The organic layer was separated and the aqueous phase was extracted twice with ethyl acetate. The combined organic phase was washed with water (twice) and brine, dried (sodium sulfate) and concentrated in vacuo to dryness to afford a solid residue, 0.941 g of crude product.

The above reaction sequence was repeated on 1.150 g (3.43 mmole) of 4,5-bis(phenylmethoxy)-2-pyridinecarboxylic acid to afford 1.120 g of crude product. The two batches of crude product were combined and triturated three times with ether. The solid was dried in vacuo to afford 1.934 g of the title compound.

(G) (2S-trans)-[1-[[2-[4,5-Bis(phenylmethoxy)-2-pyridinyl]-2-oxoethoxy]hydroxyphosphinyl]-2-methyl-4-oxo-3-azetidinyl]carbamic acid, 1,1,-dimethylethyl ester, monopotassium salt A mixture of (3S-trans)-[4-methyl-2-oxo-3-[[(1,1-dimethylethoxy)carbonyl]amino]-1-azetidinyl]phosphonic acid, methyl ester, tetrabutylammonium salt (268 mg, 0.50 mmole) and 2-(chloroacetyl)-4,5-bis(-phenylmethoxy)pyridine (217 mg, 0.59 mmole) in 3 ml of dry 1,1,1-trichloroethane was heated to reflux with stirring under nitrogen. After 38 hours, the volume was reduced by two-thirds under a nitrogen stream and reflux was continued for an additional seven hours. The mixture was cooled and concentrated in vacuo and the brown residue was dissolved in acetonitrile-water and passed through a column (2.5×22 cm) of Dowex 50X2 resin (K+ form)* packed in acetonitrile-water 20–80 and eluted with same. The relevant fractions were combined and lyophilized to afford 260 mg of crude product as a yellow solid. The above procedure was repeated using 1.181 g (2.207 mmole) of (3S-trans)-[4-methyl-2-oxo-3-[[(1,1-dimethylethoxy)carbonyl]amino]-1-azetidinyl]phosphonic acid, methyl ester, tetrabutylammonium salt and 0.883 g (2.402 mmole) of 2-(chloroacetyl)-4,5-bis-(phenylmethoxy)pyridine to afford 1.233 g of crude product. The two batches of crude product were combined, dissolved in acetonitrile-water and chromatographed on a column (5×40 cm) of CHP20P reverse phase resin** eluting with acetonitrile-water. Desired material eluted with acetonitrile-water 30–70 to 40–60. The appropriate fractions were combined and lyophilized to afford the title compound as a white solid; 1.029 g.

*Dowex 50X2 resin is a strongly acidic cation exchange resin (H) (2S-trans)-[1-[[2-(1,4-dihydro-5-hydroxy-4oxo-2-pyridinyl)-2-oxoethoxy]hydroxyphosphinyl]-2-methyl-4-oxo-3-azetidinyl]carbamic acid, 1,1-dimethylethyl ester, monopotassium salt A mixture of (2S-trans)-[1-[[2-[4,5-bis(phenylmethoxy)-2-pyridinyl]-2-oxoethoxy]hydroxyphosphinyl]-2-methyl-4-oxo-3-azetidinyl]carbamic acid, 1,1-dimethylethyl ester, monopotassium salt (60 mg, 0.092 mmole) and palladium on charcoal (7.5 mg) was stirred in 2 ml of dimethylformamide under one atmosphere of hydrogen at room temperature. After one-half hour, TLC and hydrogen uptake indicated completion of the reaction. The catalyst was separated by centrifugation and the dimethylformamide supernate was concentrated in vacuo to an oily residue. The above procedure was repeated on a larger scale ((2S-trans)-[1-[[2-[4,5-bis(phenylmethoxy)-2-pyridinyl]-2-oxoethoxy]hydroxyphosphinyl]-2-methyl-4-oxo-3-azetidinyl]carbamic acid, 1,1-dimethylethyl ester, monopotassium salt, 505 mg, 0.777 mmole; palladium on charcoal, 50 mg; dimethylformamide, 16 ml; run time 1.25 hour). The two batches of oily product were combined in 3 ml of dimethylformamide, to which was added 10 ml of ether in a fast stream. The resultant solid was separated by centrifugation, washed three times with ether, and dried in vacuo to afford 385 mg of the title compound.

**CHP20P reverse phase resin (Mitsubishi Chemical Industries, Ltd., Japan) is a styrene and divinylbenzene copolymer in a bead form having a macroreticular structure.

(I) (2S-trans)-3-Amino-2-methyl-4-oxo-1-azetidinephosphonic acid, 2-(1,4-dihydro-5-hydroxy-4-oxo-2-pyridinyl)-2-oxoethyl ester, trifluoroacetate salt Trifluoroacetic acid (3 ml) was added to a 5° C. stirred suspension of (2S-trans)-[1-[[2-(1,4-dihydro-5-hydroxy-4-oxo-2-pyridinyl)-2-oxoethoxy]hydroxyphosphinyl]-2-methyl-4-oxo-3-azetidinyl]carbamic acid, 1,1-dimethylethyl ester, monopotassium salt (375 mg) in 4 ml of dry dichloromethane containing 1 ml of anisole. After about three minutes, the solid dissolved and the mixture was stirred for 1.25 hours at 5° C. TLC indicated the reaction was essentially complete. Toluene (2 ml) was added and the mixture was concentrated in vacuo to a viscous brown oil. The oil was washed twice with hexane, then triturated with ether. The resultant solid was washed twice with ether and dried in vacuo to afford 0.437 g of crude title compound, which was used directly in the next step.

(J) [2S-[2α,3β(Z)]]-2-[[[1-(2-Amino-4-thiazolyl)-2-[[1-[[2-[(1,4-dihydro-5-hydroxy-4-oxo-2-pyridinyl)-2-oxoethoxy]hydroxyphosphinyl]-2-methyl-4-oxo-3-azetidinyl]amino]-2-oxoethylidene]amino]-oxy]-2-methylpropanoic acid, diphenylmethyl ester, potassium salt To a solution of (Z)-2-amino-α-[[2-(diphenylmethoxy)-1,1-dimethyl-2-oxoethoxy]imino]-4-thiazoleacetic acid (383 mg, 0.816 mmole) and N-hydroxybenzotriazole (110 mg, 0.814 mmole) in 2 ml of dry dimethylformamide was added dicyclohexylcarbodiimide (183 mg, 0.888 mmole). After a few minutes of stirring, a large amount of precipitate separated. The mixture was stirred for 0.5 hours at room temperature. In a separate flask, diisopropylethylamine (502 μl, 2.88 mmole) was added to a solution of (2S-trans)-3-amino-2-methyl-4-oxo-1-azetidinephosphonic acid, 2-(1,4-dihydro-5-hydroxy-4-oxo-2-pyridinyl)-2-oxoethyl ester, trifluoroacetate salt (415 mg) in 2.5 ml of dimethylformamide at 0° C. To this stirred mixture was added the mixture of the side chain active ester. The reaction mixture was stirred overnight at room temperature. The solid was separated by centrifugation and the supernate was concentrated to a thick brown gum which was taken up in 6 ml of acetonitrile-water (1:1). Additional solid was separated and the supernate was passed through a column (2.5×40 cm) of Dowex 50X2 (K+ form), eluting with acetonitrile-water 20–80. Combination and lyophilization of the appropriate fractions afforded 570 mg of an orange solid. This was dissolved in 4 ml of water (pH of solution, 6.80) and chromatographed on a column (2.5×40 cm) of CHP20P reverse phase resin. The column was eluted with water then acetonitrile-water in a stepwise gradient. Desired material was eluted with acetonitrile-water 20–80. The appropriate fractions were combined and lyophilized to afford 109 mg of the title compound as a white solid.

(K) [2S-[2α,3β(Z)]]-2-[[[1-(2-Amino-4-thiazolyl)-2-[[1-[[2-[(1,4-dihydro-5-hydroxy-4-oxo-2-pyridinyl)-2-oxoethoxy]hydroxyphosphinyl]-2-methyl-4-oxo-3-azetidinyl]amino]-2-oxoethylidene]amino]-oxy]-2-methylpropanoic acid Trifluoroacetic acid (4 ml) was added dropwise to a 5° C. stirred suspension of [2S-[2α,3β(Z)]]-2-[[[1-(2-amino-4-thiazolyl)-2-[[1-[[2-[(1,4-dihydro-5-hydroxy-4-oxo-2-pyridinyl)-2-oxoethoxy]hydroxyphosphinyl]-2-methyl-4-oxo-3-azetidinyl]amino]-2-oxoethylidene]amino]-oxy]-2-methylpropanoic acid, diphenylmethyl ester, potassium salt (109 mg, ca. 0.138 mmole) in 3 ml of dry dichloromethane containing 0.3 ml of anisole. After stirring at 5° C. for 45 minutes, 2 ml of toluene was added and the mixture was concentrated to a thick oil. The oil was washed twice with hexane and was triturated with ether, whereupon it solidified. The solid was washed with ether and dried in vacuo to afford 100 mg of crude product. This was dissolved in 2 ml of water (pH of solution 2.70) and chromatographed on a column (1.5×26 cm) of CHP20P reverse phase resin. The column was eluted with water then acetonitrile-water in a stepwise gradient. Desired material eluted with acetonitrile-water (5–95). The appropriate fractions were combined and lyophilized to afford 53 mg of the title product as a white solid. In water, the title product exists as a ca. 1:2 mixture of ketone and ketone hydrate.

EXAMPLE 2

[2S-[2α,3β(Z)]]-2-[[[1-(2-Amino-4-thiazolyl)-2-[[1-[[(1,4-dihydro-5-hydroxy-4-oxo-2-pyridinyl)-methoxy]hydroxyphosphinyl]-2-methyl-4-oxo-3-azetidinyl]amino]-2-oxoethylidene]amino]oxy]-2-methylpropanoic acid (A) 2-(Hydroxymethyl)-5-(phenylmethoxy)-1-(phenylmethyl)-4(1H)-pyridinone A solution of 2-(hydroxymethyl)-5-(phenylmethoxy)-4H-pyran-4-one (10.5 g, 45.3 mmol) in benzylamine (40 ml) and water (60 ml) was refluxed for four hours and then stirred overnight at room temperature. The resulting precipitate was collected and washed thoroughly with water to give 9.17 g (28.6 mmol) of 2-(hydroxymethyl)-5-(phenylmethoxy)-1-(phenylmethyl)-4(1H)pyridinone (melting point 146°–147° C.) upon drying. The supernatant was diluted with water to a total volume of 450 ml, and after standing for one hour at room temperature, the resulting precipitate was collected to yield 2.47 g (7.69 mmol) of additional 2-(hydroxymethyl)-5-(phenylmethoxy)-1-(phenylmethyl)-4(1H)-pyridinone upon drying.

(B) 2-[(Methylsulfonyl)oxy]-5-(phenylmethoxy)-1-(phenylmethyl)-4(1H)pyridinone

To a suspension of 2-(hydroxymethyl)-5-(phenylmethoxy)-1-(phenylmethyl)-4(1H)-pyridinone (4.66 g, 14.5 mmol) in dichloromethane (43 ml) at 0° C. was added triethylamine (3.0 ml) followed by methanesulfonyl chloride (1.24 ml). After 0.5 hours, another 1.5 ml of triethylamine was added followed by 0.62 ml of methanesulfonyl chloride.

After 0.5 hours at 0° C., the reaction mixture was poured into 75 ml of water and the methylene chloride was removed in vacuo. The resulting solid was filtered and washed several times with cold ethyl acetate to yield 4.86 g of the title compound as a light pink solid, melting point 115°–117° C.

(c) (2S-trans)-[1-[[[1,4-Dihydro-4-oxo-5-(phenylmethoxy)-1-(phenylmethyl)-2-pyridinyl]methoxy]hydroxyphosphinyl]-2-methyl-4-oxo-3-azetidinyl]carbamic acid, 1,1-dimethylethyl ester, monopotassium salt A solution of (3S-trans)-2-oxo-3-[[(1,1-dimethylethoxy)carbonyl]amino]-1-azetidinyl]phosphonic acid, methyl ester, tetrabutylammonium salt (2.95 g, 5.5 mmol), 2-[(methylsulfonyl)oxy]-5-(phenylmethoxy)-1-(phenylmethyl)-4(1H)pyridinone (2.60 g, 6.5 mmol), and tetrabutylammonium bromide (1.77 g, 5.5 mmol) in 44 ml of 1,1,1-trichloroethane was boiled over a period of 30 minutes while evaporating ~15 ml of the solvent. 1,1,1-Trichloroethane (15 ml) was then added back to the reaction and the mixture was refluxed for 4.5 hours. The volatiles were then removed and the residue was applied to a Dowex 50X2 resin (K+ form) column (eluting with 20% acetonitrile-water). The appropriate fractions were combined, slurried with additional Dowex 50X2 resin (K+ form), and finally filtered. Upon freeze drying, the residue was purified by chromatography on CHP20P reverse phase resin eluting with acetonitrile-water yielding 2.33 g of the title compound.

(D) (2S-trans)-[1-[[(1,4-Dihydro-5-hydroxy-4-oxo-2-pyridinyl)methoxy]hydroxyphosphinyl]-2-methyl-4-oxo-3-azetidinyl]carbamic acid, monopotassium salt (2S-trans)-[1-[[[1,4-Dihydro-4-oxo-5-(phenylmethoxy)-1-(phenylmethyl)-2-pyridinyl]methoxy]hydroxyphosphinyl]-2-methyl-4-oxo-3-azetidinyl]carbamic acid, 1,1-dimethylethyl ester, monopotassium salt (932 mg, 1.5 mmol) was hydrogenolyzed in 15 ml of dimethylformamide in the presence of p-toluenesulfonic acid, monohydrate (285 mg, 1.5 mmol) using 10% palladium on charcoal (466 mg) as the catalyst. After 30 minutes, 15 ml of water was added and the catalyst was filtered off. The volatiles were removed from the supernatant, the residue was dissolved in water and the pH adjusted to 5.0 (using aqueous potassium bicarbonate), and this solution was finally chromatographed on a column of CHP20P reverse phase resin (eluting with water and 5% acetone-water) yielding 494 mg of the title compound upon lyophilization.

(E) [2S-[2α,3β(Z)]]-2-[[[1-(2-Amino-4-thiazolyl)-2-[[1-[-[(1,4-dihydro-5-hydroxy-4-oxo-2-pyridinyl)methoxy]hydroxyphosphinyl]-2-methyl-4-oxo-3-azetidinyl]amino]-2-oxoethylidene]amino]oxy]-2-methylpropanoic acid, diphenylmethyl ester, potassium salt (2S-trans)-1-[[(1,4-Dihydro-5-hydroxy-4-oxo-2-pyridinyl)methoxy]hydroxyphosphinyl]-2-methyl-4-oxo-3-azetidinyl]carbamic acid, monopotassium salt (265 mg, 0.6 mmol) was suspended in dichloromethane (1.6 ml) and anisole (0.46 ml) and cooled to 0° C. Trifluoroacetic acid (2.0 ml) was added, and the reaction was stirred for one hour. Toluene (1.0 ml) was added, and the volatiles were removed under vacuum without external heat. The residue was triturated with hexane and then dry ether to give the deprotected azetidinone as a powder upon evacuation.

The N-hydroxybenzotriazole ester of (Z)-2-amino-α-[[2-(diphenylmethoxy)-1,1-dimethyl-2-oxoethoxy]imino]-4-thiazoleacetic acid was prepared by dissolving an isopropanol solvate of the acid (338 mg, 0.72 mmol) in dimethylformamide (1.5 ml), cooling to 0° C., and adding N-hydroxybenzotriazole monohydrate (110 mg, 0.72 mmol) followed by dicyclohexylcarbodiimide (148 mg, 0.72 mmol). This was stirred at 0° C. for one hour.

The deprotected azetidinone was dissolved in 1.5 ml of water. The pH was adjusted to 6.0 with solid potassium bicarbonate. The above N-hydroxybenzotriazole ester of (Z)-2-amino-α-[[2-(diphenylmethoxy)-1,1-dimethyl-2-oxoethoxy]imino]-4-thiazoleacetic acid was added, resulting in the formation of considerable precipitate. Another 2.0 ml of dimethylformamide was added to the reaction mixture to dissolve most of the precipitate, and the pH was kept between 6.5–7.0 with aqueous potassium bicarbonate.

After one hour at 0° C., additional N-hydroxybenzotriazole ester of (Z)-2-amino-α-[[2-(diphenylmethoxy)-1,1-dimethyl-2-oxoethoxy]imino]-4-thiazoleacetic acid was added to the reaction mixture. After 30 minutes, the reaction was filtered, and the volatiles were removed. The residue was dissolved in water (pH 5.4) and chromatographed on a column of CHP20P reverse phase resin (eluting with acetone-water). The appropriate fractions were combined to yield the title compound (232 mg, 0.304 mmol) upon lyophilization.

(F) [2S-[2α,3β(Z)]]-2[[[1-(2-Amino-4-thiazolyl)-2-[[1-[-[(1,4-dihydro-5-hydroxy-4-oxo-2-pyridinyl)methoxy]hydroxyphosphinyl]-2-methyl-4-oxo-3-azetidinyl]amino]-2-oxoethylidene]amino]oxy]-2-methylpropanoic acid

[2S-[2α,3β(Z)]]-2-[[[1-(2-Amino-4-thiazolyl)-2-[[-1-[[(1,4-dihydro-5-hydroxy-4-oxo-2-pyridinyl)methoxy]hydroxyphosphinyl]-2-methyl-4-oxo-3-azetidinyl]amino-2-oxoethylidene]amino]oxy]-2-methylpropanoic acid, diphenylmethyl ester, potassium salt (220 mg, 0.29 mmol) was suspended in 3 ml of dichloromethane and 0.3 ml of anisole. Upon cooling to 0° C., 4.7 ml of trifluoroacetic acid was added. After 30 minutes, 2 ml of toluene was added, and the volatiles were removed without external heat. The residue was triturated with hexane followed by dry ether to give a solid upon evacuation. An aqueous solution of this solid was adjusted to pH 2.5 with aqueous potassium bicarbonate and chromatographed on a column of CHP20P reverse phase resin (eluting with acetone-water) to give 45 mg (0.081 mmol) of the title product upon lyophilization.

EXAMPLE 3

[2S-[2α,3β(Z)]]-2-[[[1-(2-Amino-4-thiazolyl)-2-[[1-[[-2-[(3,4-dihydroxyphenyl)amino]-2-oxo-ethoxy]hydroxyphosphinyl]-2-methyl-4-oxo-3-azetidinyl]amino]-2-oxoethylidine]amino]oxy]-2-methylpropanoic acid (A) 2-Chloro-N-[3,4-bis(phenylmethoxy)phenyl]acetamide To 7.7 g (25 mmol) of 3,4-dibenzyloxyaniline in 50 ml of 1:1 acetonitrile/water at 0° C. was added chloroacetyl chloride (3.0 ml) while keeping the pH at 6.5 with saturated aqueous potassium bicarbonate. When the pH remained constant for 15 minutes, an additional 3 ml of chloroacetyl chloride was added in small portions while maintaining the pH at 6.5. When the pH remained constant for 15 minutes, the acetonitrile was evaporated, and the resulting aqueous solution was filtered. The precipitate was washed thoroughly with water to yield, upon drying in vacuo, 8.98 g of the title compound.

(B) 2-Iodo-N-[3,4-bis(phenylmethoxy)phenyl]acetamide

A solution of 2-chloro-N-[3,4-bis(phenylmethoxy)phenyl]acetamide (8.98 g, 23.5 mmol) and sodium iodide (3.53 g, 23.5 mmol) in acetone (75 ml) was refluxed for two hours and allowed to stand overnight at room temperature. The reaction was filtered hot to remove the sodium iodide and a precipitate formed in the cold filtrate which was collected and washed with cold acetone to give, upon drying, 6.71 g (14.2 mmol) of the title compound. A second crop was obtained from cold acetone (1.0 g).

(C) (2S-trans)-[1-[[2-[[3,4-bis(phenylmethoxy)phenyl]amino]-2-oxoethoxy]hydroxyphosphinyl]-2-methyl-4-oxo-3-azetidinyl]carbamic acid, 1,1-dimethylethyl ester, monopotassium salt A solution of (3S-trans)-2-oxo-3-[[(1,1-dimethylethoxy)carbonyl]amino]-1-azetidinyl]phosphonic acid, methyl ester, tetrabutylammonium salt (4.32 g, 8.0 mmol) and 2-iodo-N-[3,4-bis-(phenylmethoxy)phenyl]acetamide (7.60 g, 16 mmol) in 80 ml of 1,1,1-trichloroethane was refluxed for 6 hours. After 25 ml of solvent was evaporated over one hour at ambient pressure (bath temperature of 85° C.), the reaction mixture was brought back to its original volume with 1,1,1-trichloroethane and refluxed overnight.

The volatiles were removed under vacuum, and a Dowex 50X2 resin (K+ form) column was run on the residue (eluting with water). The appropriate fractions were combined, slurried with additional Dowex 50X2 resin (K+ form), filtered, and freeze dried. Purification of the residue on CHP20P reverse phase resin (eluting with acetone-water) yielded, upon freeze drying, 2.97 g (4.48 mmol) of the title compound.

(D) (2S-trans)-[1-[[2-[(3,4-dihydroxyphenyl)amino]-2-oxoethoxy]hydroxyphosphinyl]-2-methyl-4-oxo-3- azetidinyl]carbamic acid, 1,1-dimethylether ester, monopotassium salt

A solution of (2S-trans)-[1-[[2-[[3,4-bis-(phenylmethoxy)phenyl]amino]-2-oxoethoxy]hydroxyphosphinyl]-2-methyl-4-oxo-3-azetidinyl]carbamic acid, 1,1-dimethylethyl ester, monopotassium salt (2.97 g, 4.48 mmol) in 30 ml of 1:1 acetonitrile/water in the presence of 10% palladium on charcoal (1.5 g) was hydrogenolyzed at room temperature and one atmosphere for 105 minutes. The reaction mixture was filtered, and the volatiles were removed. An aqueous solution of the residue was adjusted to pH 3 with dilute hydrochloric acid and chromatographed on a column of Dowex 50X2 resin (K+ form) (eluting with water). The appropriate fractions were combined and the volatiles were removed. An aqueous solution of the residue was adjusted to pH 7 with aqueous potassium bicarbonate and chromatographed on CHP20P reverse phase resin (eluting with acetone-water) to give, upon freeze drying, 1.895 g (3.92 mmol) of the title compound.

(E) [2S-[2α,3β(Z)]]-2-[[[1-(2-Amino-4-thiazolyl)-2-[[1--[[2-[3,4-dihydroxyphenyl)amino]-2-oxoethoxy]hydroxyphosphinyl]-2-methyl-4-oxo-3-azetidinyl]amino]-2-oxoethylidene]amino]oxy]-2-methylpropanoic acid, diphenylmethyl ester, potassium salt (2S-trans)-[1-[[2-[(3,4-dihydroxyphenyl)amino]-2-oxoethoxy]hydroxyphosphinyl]-2-methyl-4-oxo-3-azetidinyl]-carbamic acid, 1,1-dimethylethyl ester, monopotassium salt was suspended in dichloromethane (1.6 ml) and anisole (0.46 ml) and cooled to 0° C. Trifluoroacetic acid (2.0 ml) was added, and the reaction was stirred for 30 minutes. Toluene (1.0 ml) was added, and the volatiles were removed under vacuum without external heat. The residue was triturated with hexane and then dry ether to give the deprotected azetidinone as a powder upon evacuation.

The N-hydroxybenzotriazole ester of (Z)-2-amino-α-[[2-(diphenylmethoxy)-1,1-dimethyl-2-oxoethoxy]imino]-4-thiazoleacetic acid was prepared by dissolving an isopropanol solvate of the acid (310 mg, 0.66 mmol) in dimethylformamide (1.5 ml), cooling to 0° C., and adding N-hydroxybenzotriazole monohydrate (1.01 mg, 0.66 mmol) followed by dicyclohexylcarbodiimide (136 mg, 0.66 mmol). This was stirred at 0° C. for one hour.

The deprotected azetidinone was dissolved in 1.5 ml of dimethylformamide at 0° C. The above N-hydroxybenzotriazole ester in dimethylformamide was then added followed by 0.314 ml (1.8 mmol) of diisopropylethylamine. After stirring for 6.5 hours at 0° C., the reaction was filtered through Celite, and the volatiles were removed. The residue was chromatographed on Dowex 50X-2 (K+ form) (eluting with water). The appropriate fractions were combined, and the volatiles were removed. The residue was purified on CHP20P reverse phase resin (eluting with acetone-water) to give, upon freeze drying, the title compound.

(F) [2S-[2α,3β(Z)]]-2-[[[1-(2-Amino-4-thiazolyl)-2-[[1--[[2-[(3,4-dihydroxyphenyl)amino]-2-oxoethoxy]ydroxyphosphinyl]-2-methyl-4-oxo-3-azetidinyl]mino]-2-oxoethylidene]amino]oxy]-2-methylropanoic acid

[2S-[2α,3β(Z)]]-2-[[[1-(2-Amino-4-thiazolyl)-2-[[1-[-2-[(3,4-dihydroxyphenyl)amino]-2-oxoethoxy]hydroxyphosphinyl]-2-methyl-4-oxo-3-azetidinyl]amino]-2-oxoethylidene]amino]oxy]-2-methylpropanoic acid, diphenylmethyl ester, potassium salt was suspended in 3 ml of dichloromethane and 0.3 ml of anisole. Upon cooling to 0° C., 4.7 ml of trifluoroacetic acid was added. After 45 minutes, 2.0 ml of toluene was added and the volatiles were removed without external heat. The residue was triturated with hexane followed by dry ether to give, upon evacuation, an off-white solid. An aqueous solution of the residue was adjusted to pH 2.5 with aqueous sodium bicarbonate and chromatographed on CHP20P reverse phase resin (eluting with water and 10% acetone-water) to give, upon freeze drying, 225 mg of the title product.

EXAMPLE 4

[2S-[2α,3β(Z)]]-2-[[[1-(2-Amino-4-thiazolyl)-2-[[1-[[2-[2-[(1,4-dihydro-5-hydroxy-2-pyridinyl)carbonyl]hydrazino]-2-oxoethoxy]hydroxyphosphinyl]-2-methyl-4-oxo-3-azetidinyl]amino]-2-oxoethylidene]amino]oxy]-2-methylpropanoic acid (A) (2S-trans)-[1-[(2-Hydrazino-2-oxoethoxy)hydroxyphosphinyl]-2-methyl-4-oxo-3-azetidinyl]carbamic acid, 1,1-dimethylethyl ester, monopotassium salt To a stirred solution of (2S-trans)-[1-[hydroxy[2-oxo-2-(phenylmethoxy)ethoxy]phosphinyl]-2-methyl-4-oxo-3-azetidinyl]carbamic acid, 1,1-dimethylethyl ester, monopotassium salt (1.87 g, 4.0 mmol) in 20 ml of dry acetonitrile was added one equivalent of hydrazine (7.89M solution in acetonitrile) and the mixture was stirred overnight (18 hours) at room temperature. The desired product precipitated from solution. The acetonitrile was decanted and the glass-like precipitate was triturated with additional acetonitrile (10 ml) followed by trituration with ether (2×10 ml). The solid was dried in vacuo yielding 1.38 g of crude material. The material was dissolved in 10 ml of water and purified on a 150 ml CHP20P reverse phase column eluting with water. The appropriate fractions were combined and lyophilized to yield 1.16 g of the title compound.

(B) (2S-trans)-[1-[[2-[2-[[1,4-Dihydro-4-oxo-5-(phenylmethoxy)-2-pyridinyl)carbonyl]hydrazino]-2-oxoethoxy]hydroxyphosphinyl]-2-methyl-4-oxo-3-azetidinyl]carbamic acid, 1,1-dimethylethyl ester, monopotassium salt To a solution of 1,4-dihydro-4-oxo-5-(phenylmethoxy)-2-pyridinecarboxylic acid (525 mg, 2.14 mmol) and N-hydroxybenzotriazole (289 mg, 2.14 mmol) in 6 ml of dry dimethylformamide was added N,N'-dicyclohexylcarbodiimide (442 mg, 2.14 mmol) and the resulting mixture was stirred at room temperature, under argon, for 45 minutes. A separate solution of (2S-trans)-[1-[(2-hydrazino-2-oxoethoxy)hydroxyphosphinyl]-2-methyl-4-oxo-3-azetidinyl]carbamic acid, 1,1-dimethylethyl ester, monopotassium salt (749 mg, 2.0 mmol) in 5 ml of dimethylformamide was added to the dimethylformamide solution containing the active ester and the resulting mixture was stirred overnight (18 hours) at room temperature. The precipitated dicyclohexylurea was removed by filtration and the dimethylformamide was evaporated in vacuo yielding a pale yellow residue. The residue was dissolved in 10 ml of water and the pH adjusted to pH 6.4 with potassium bicarbonate. The aqueous mixture was purified on a 150 ml CHP20P reverse phase column eluting with a gradient of acetonitrile-water. The appropriate fractions were combined, concentrated and finally lyophilized to yield 980 mg of the desired coupled material (2S-trans)-[1-[[2-[2-[[1,4-dihydro-4-oxo-5-(phenylmethoxy)-2-pyridinyl)carbonyl]hydrazino]-2-oxoethoxy]hydroxyphosphinyl]-2- methyl-4-oxo-3-azetidinyl]carbamic acid, 1,1-dimethylethyl ester, monopotassium salt as a white solid.

(C) (2S-trans)-[1-[[2-[2-[(1,4-Dihydro-5-hydroxy-4-oxo-2-pyridinyl)carbonyl]hydrazino]-2-oxoethoxy]hydroxyphosphinyl-2-methyl-4-oxo-3-azetidinyl]carbamic acid, 1,1-dimethylethyl ester, monosodium salt A solution of (2S-trans)-[1-[[2-[2-[[1,4-dihydro-4-oxo-5-(phenylmethoxy)-2-pyridinyl)carbonyl]hydrazino]-2-oxoethoxy]hydroxyphosphinyl]-2-methyl-4-oxo-3-azetidinyl]carbamic acid, 1,1-dimethylethyl ester, monopotassium salt (926 mg, 1.5 mmol) in 4 ml of dry dimethylformamide was stirred under a hydrogen atmosphere with 500 mg of 10% palladium on charcoal for two hours at room temperature. The mixture was filtered through Celite and the filtrate was evaporated in vacuo at room temperature yielding a yellow oily residue. The residue was triturated with hexanes (2×10 ml) followed by trituration with ether (3×10 ml) yielding 680 mg of the title compound as a colorless solid.

(D) (2S-trans)-(3-Amino-2-methyl-4-oxo-1-azetidinyl)-phosphonic acid, 2-[2-[[(1,4-dihydro-5-hydroxy-4-oxo-2-pyridinyl)carbonyl]hydrazino]-2-oxoethyl ester, 1.0 trifluoroacetate salt To a suspension of (2S-trans)-[1-[[2-[2-[(1,4-dihydro-5-hydroxy-4-oxo-2-pyridinyl)carbonyl)hydrazino]-2-oxoethoxy]hydroxyphosphinyl]-2-methyl-4-oxo-3-azetidinyl]carbamic acid, 1,1-dimethylethyl ester, monosodium salt (660 mg, 1.25 mmol) in 15 ml of dry dichloromethane was added 1 ml of anisole and the mixture was then cooled to −10° C. in an ice-alcohol bath under argon. Trifluoroacetic acid (4 ml) was added and the mixture stirred for two hours. After stirring for 15 minutes at −10° C., the mixture was warmed to 0° C. for the remainder of the time. The mixture was diluted with 10 ml of dry toluene and the solvents were removed in vacuo at room temperature yielding a yellow oily residue. The residue was triturated with hexanes (2×10 ml) followed by trituration with ether (3×10 ml). The resulting solid was dried in vacuo yielding (2S-trans)-(3-amino-2-methyl-4-oxo-1-azetidinyl)phosphonic acid, 2-[2-[[(1,4-dihydro-5-hydroxy-4-oxo-2-pyridinyl)carbonyl]hydrazino]-2-oxoethyl ester, 1.0 trifluoroacetate salt. The material was used immediately in the next step without further purification.

(E) [2S-[2α,3β(Z)]]-2-[[[1-(2-Amino-4-thiazolyl)-2-[[1-[[2-[2-[(1,4-dihydro-5-hydroxy-2-pyridinyl)carbonyl]hydrazino]-2-oxoethoxy]hydroxyphosphinyl]-2-methyl-4-oxo-3-azetidinyl]amino]-2-oxoethylidene]amino]oxy]-2-methylpropanoic acid, diphenylmethyl ester, sodium salt (Z)-2-Amino-α-[[2-(diphenylmethoxy)-1,1-dimethyl-2-oxoethoxy]imino]-4-thiazole acetic acid (527 mg, 1.3 mmol) and one equivalent of N-hydroxybenzotriazole (176 mg, 1.3 mmol) were dissolved in 3 ml of dry dimethylformamide under argon atmosphere. N,N'-Dicyclohexylcarbodiimide (268 mg, 1.3 mmol) was added to the solution and the resulting mixture was stirred for 30 minutes. A separate solution of (2S-trans)-(3-amino-2-methyl-4-oxo-azetidinyl)phosphonic acid, 2-[2-[[(1,4-dihydro-5-hydroxy-4-oxo-2-pyridinyl)carbonyl]hydrazino]-2-oxoethyl ester, trifluoroacetate salt (1.25 mmol) in 3 ml of dimethylformamide was treated with diisopropylethylamine (792 µl, 4.55 mmol) and was added to the solution of the side chain ester. The reaction mixture was then stirred for 26 hours at room temperature. The dimethylformamide was removed in vacuo at 25° C. and the resulting residue was partially dissolved in a 40% acetonitrile/water solution (75 ml) and the pH adjusted to pH 6.2 with sodium bicarbonate solution. Dowex (Na+ form) ion-exchange resin (75 ml) was added to the solution and the mixture was then stirred for 30 minutes, filtered and the acetonitrile removed in vacuo. The water was lyophilized yielding the crude coupled product as the sodium salt. The crude material was dissolved in 10 ml of water and was purified on a column (125 ml) of CHP20P reverse phase resin. The column was eluted with an acetonitrile-water gradient. The desired product eluted from the column in approximately 35% acetonitrile/water. The appropriate fractions were combined, the acetonitrile removed in vacuo and the water lyophilized to yield 405 mg of the title compound as a colorless solid.

(F) [2S-[2α,3β(Z)]]-2-[[[1-(2-Amino-4-thiazolyl)-2-[[1-[[2-[2-[(1,4-dihydro-5-hydroxy-2-pyridinyl)carbonyl]hydrazino]-2-oxoethoxy]hydroxyphosphinyl]-2-methyl-4-oxo-3-azetidinyl]amino]-2-oxoethylidene]amino]oxy]-2-methylpropanoic acid To a suspension of [2S-[2α,3β(Z)]]-2-[[[1-(2-amino-4-thiazolyl)-2-[[1-[[2-[2-[(1,4-dihydro-5-hydroxy-2--pyridinyl)carbonyl]hydrazino]-2-oxoethoxy]hydroxyphosphinyl]-2-methyl-4-oxo-3-azetidinyl]amino]-2-oxo-ethylidene]amino]oxy]-2-methylpropanoic acid, diphenylmethyl ester, sodium salt (398 mg, 0.475 mmol) in 4 ml of dry, distilled dichloromethane was added 0.6 ml of anisole and the mixture cooled to −5° C. in an ice/methanol bath. With stirring and under an argon atmosphere, 8 ml of trifluoroacetic acid was added and the mixture was stirred at 0° C. for two hours. Toluene (8 ml) was added and the solvents were removed in vacuo at 20° C. yielding a pale yellow oily residue. The residue was triturated with hexanes (2×15 ml) followed by trituration with dry ether (3×15 ml) yielding the trifluoroacetate salt of crude product as a colorless solid. The salt was dissolved in 6 ml of water and the pH adjusted to pH 2.5 with sodium bicarbonate solution. The aqueous mixture was purified on a 40 ml CHP20P reverse phase resin column, eluting with an acetonitrile-water gradient. The product eluted from the column in approximately 30% acetonitrile/water. The appropriate fractions were combined, the acetonitrile removed in vacuo and the water lyophilized to yield 192 mg of the title product as a colorless solid.

EXAMPLE 5

[2S-[2α,3β(Z)]]-2-[[[1-(2-Amino-4-thiazolyl)-2-[[1-[[2-[[(1,4-dihydro-5-hydroxy-4-oxo-2-pyridinyl)-methyl]amino]-2-oxoethoxy]hydroxyphosphinyl]-2-methyl-4-oxo-3-azetidinyl]amino]-2-oxoethylidene]-amino]oxy]-2-methylpropanoic acid (A) (2S-trans)-[1-[Hydroxy[2-oxo-2-(phenylmethoxy)ethoxy]phosphinyl]-2-methyl-4-oxo-3-azetidinyl]carbamic acid, 1,1-dimethylethyl ester, monopotassium salt (3S-trans)-4-Methyl-2-oxo-3-[[(1,1-dimethylethoxy)-carbonyl]amino]-1-azetidinyl]phosphonic acid, methyl ester, tetrabutylammonium salt (8.1 g, 15.1 mmol) was dissolved in 150 ml of 1,1,1-trichloroethane and treated with benzyl bromoacetate (6.88 g, 30 mmol). The solution was warmed to reflux for 4.5 hours. The reaction mixture was cooled to room temperature and evaporated in vacuo to give a yellow oil. The oil was applied to a Dowex 50X2 resin (K+ form) column and eluted with water. The appropriate fractions were combined and evaporated to ∼100 ml in vacuo and the remaining aqueous solution was lyophilized. The crude lyophilate was chromatographed on CHP20P reverse phase resin (eluting with acetone/water) to give 3.8 g of the title compound as a white solid.

(B) (2S-trans)-[1-[[2-[[[1,4-Dihydro-4-oxo-5-(phenylmethoxy)-2-pyridinyl]methyl]amino]-2-oxoethoxy]hydroxyphosphinyl]-2-methyl-4-oxo-3-azetidinyl]carbamic acid, 1,1-dimethylethyl ester, monopotassium salt A solution of (2S-trans)-[1-[hydroxy[2-oxo-2-(phenylmethoxy)ethoxy]phosphinyl]-2-methyl-4-oxo-3-azetidinyl]carbamic acid, 1,1-dimethylethyl ester, monopotassium salt (0.911 g, 2.0 mmol) in 15 ml of dry dimethylformamide was treated with 2-(aminomethyl)-1,4-dihydro-4-oxo-5-(phenylmethoxy)pyridine (0.450 g, 2.0 mmol) and warmed to 75° C. The solution was stirred for 18 hours and the dimethylformamide was evaporated. The residue was dissolved in 20% acetonitrile/water and the pH adjusted to 5 with 0.1N hydrochloric acid. The solution was then passed through a Dowex 50X2 resin (K+ form) column (eluting with 20% acetonitrile/water). The appropriate fractions were combined, evaporated to a small volume and, finally, lyophilized. The crude lyophilate was chromatographed on CHP20P reverse phase resin (eluting with water and 10% acetone/water) to give 310 mg of the title compound.

(C) (2S-trans)-[1-[[2-[[(1,4-Dihydro-5-hydroxy-4-oxo-2-pyridinyl)methyl]amino]-2-oxoethoxy]hydroxyphosphinyl]-2-methyl-4-oxo-3-azetidinyl]carbamic acid, 1,1-dimethylethyl ester, monopotassium salt A solution of (2S-trans)-[1-[[2-[[[1,4-dihydro-4-oxo-5-(phenylmethoxy)-2-pyridinyl]methyl]amino]-2-oxoethoxy]hydroxyphosphinyl]-2-methyl-4-oxo-3-azetidinyl]carbamic acid, 1,1-dimethylethyl ester, monopotassium salt (0.470 g, 0.8 mmol) and p-toluenesulfonic acid, monohydrate (0.15 g, 0.8 mmol) in 12 ml of dimethylformamide was treated with 10% palladium on charcoal (250 mg) and hydrogenated (one atmosphere, room temperature) for one hour. The slurry was treated with water (5 ml) and filtered free of the catalyst. The filtrate was concentrated to dryness in vacuo and dissolved in 5 ml of water. The pH was adjusted to 5 with saturated sodium bicarbonate, and this solution was applied to a column of CHP20P reverse phase resin. Elution with water and 5% acetone/water gave the title compound (205 mg) as a white solid upon evaporation and lyophilization.

(D) [2S-[2α,3β(Z)]]-2-[[[1-(2-Amino-4-thiazolyl)-2-[[1-[[2-[[(1,4-dihydro-5-hydroxy-4-oxo-2-pyridinyl)methyl]amino]-2-oxoethoxy]hydroxyphosphinyl]-2-methyl-4-oxo-3-azetidinyl]amino]-2-oxoethylidene]amino]oxy]-2-methylpropanoic acid, diphenylmethyl ester, potassium salt (Z)-2-Amino-α-[[2-(diphenylmethoxy)-1,1-dimethyl-2-oxoethoxy]imino]-4-thiazoleacetic acid (185 mg, 0.41 mmol) and N-hydroxybenzotriazole (57 mg, 0.42 mmol) were dissolved in 1 ml of dimethylformamide at 0° C. To this was added dicyclohexylcarbodiimide (87 mg, 0.42 mmol), and the resulting suspension was stirred for one hour at 0° C. to give the N-hydroxybenzotriazole ester.

A suspension of (2S-trans)-[1-[[2-[[(1,4-dihydro-5-hydroxy-4-oxo-2-pyridinyl)methyl]amino]-2-oxoethoxy]hydroxyphosphinyl]-2-methyl-4-oxo-3-azetidinyl]carbamic acid, 1,1-dimethylethyl ester, monopotassium salt (190 mg, 0.38 mmol) in dichloromethane (2 ml) at 0° C. was treated sequentially with anisole (0.35 ml) and trifluoroacetic acid (1.2 ml), and the resulting solution was stirred at 0° C. for one hour. The trifluoroacetic acid was then removed in vacuo and the residue was coevaporated with toluene. The residue was then triturated with hexane and ether and finally dried in vacuo for 15 minutes to give a white solid. This solid was dissolved in dimethylformamide (1 ml) and added to the abovedescribed N-hydroxybenzotriazole ester. This mixture was then treated with 0.36 ml of diisopropylethylamine and stirred at 0° C. for 5.5 hours. The solution was warmed to room temperature, filtered through Celite, and evaporated to dryness. The residue was passed through a Dowex 50X-2 resin (K+ form) column (eluting with 10% acetonitrile/water and 20% acetonitrile/water). The appropriate fractions were combined, evaporated free of acetonitrile, and lyophilized. The lyophilate was dissolved in 5 ml of water, the pH adjusted to 5.5, and the solution chromatographed on a column of CHP20P reverse phase resin, eluting with acetone/water. Combination and lyophilization of the appropriate fraction afforded the title compound (129 mg) as a white solid.

(E) [2S-[2α,3β(Z)]]-2-[[[1-(2-amino-4-thiazolyl)-2-[[1-[[2-[[(1,4-dihydro-5-hydroxy-4-oxo-2-pyridinyl)methyl]amino]-2-oxoethoxy]hydroxyphosphinyl]-2-methyl-4-oxo-3-azetidinyl]amino]-2-oxoethylidene]amino]oxy]-2-methylpropanoic acid A suspension of [2S-[2α,3β(Z)]]-2-[[[1-(2-amino-4-thiazolyl)-2-[[1-[[2-[[(1,4-dihydro-5-hydroxy-4-oxo-2-pyridinyl)methyl]amino]-2-oxoethoxy]hydroxyphosphinyl]-2-methyl-4-oxo-3-azetidinyl]amino]-2-oxoethylidene]amino]oxy]-2-methylpropanoic acid, diphenylmethyl ester, potassium salt (120 mg, 0.14 mmol) in dichloromethane (5 ml) at 0° C. was treated sequentially with anisole (0.25 ml) and trifluoroacetic acid (3 ml) and stirred one hour at 0° C. The trifluoroacetic acid was evaporated in vacuo, and the residue coevaporated with toluene (5 ml). This residue was triturated with hexane and then with diethyl ether and the resulting off-white solid was dried in vacuo. The solid was then dissolved in water (3 ml), the pH was adjusted to 3 and the solution was chromatographed on a CHP20P reverse phase resin column (eluting with water and 5% acetone/water). The appropriate fractions were combined, evaporated free of acetone, and lyophilized to give the title product as an off-white solid, (71 mg), melting point 191° C., dec.

EXAMPLE 6

[2S-[2α,3β(Z)]]-2-[[[1-(2-Amino-4-thiazolyl)-2-[-[2-oxo-1-[[2-(3,4-dihydroxyphenyl)-2-oxoethoxy]hydroxyphosphinyl]-3-azetidinyl]amino]-2-oxoethylidene]amino]oxy]-2-methylpropanoic acid, disodium salt (A) (S)-[1-[[2-[3,4-Bis(acetyloxy)phenyl]-2-oxoethoxy]hydroxyphosphinyl]-2-oxo-3-azetidinyl]carbamic acid, 1,1-dimethylethyl ester, monosodium salt A mixture of (3S-trans)-4-methyl-2-oxo-3-[[(1,1-dimethylethoxy)carbonyl]amino]-1-azetidinyl]phosphonic acid, methyl ester, tetrabutylammonium salt (2.0 g, 3.75 mmol) and two equivalents of 3',4'-bis(acetyloxy)-2-iodoacetophenone was heated at reflux in 10 ml of 1,1,1-trichloroethane for 24 hours. The solvent was removed in vacuo and the resulting dark residue was redissolved in 25 ml of acetonitrile and the solvent again removed in vacuo removing any residual trichloroethane. The residue was dissolved in 50 ml of water and the pH adjusted to pH 6.5 with potassium bicarbonate solution. The aqueous mixture was washed with ether (3×30 ml) removing the excess iodo compound. Dowex (K+ form) ion-exchange resin (50 ml) was added to the aqueous mixture and stirred overnight. The resin was filtered, washed with additional water and the filtrate was lyophilized yielding (S)-[1-[[2-[3,4-bis(acetyloxy)-phenyl]-2-oxoethoxy)hydroxyphosphinyl]-2-oxo-3-azetidinyl]carbamic acid, 1,1-dimethylethyl ester, monosodium salt as a yellow solid. The crude product contained both diacetyl and monoacetyl protected material, as well as (S)-[1-[[2-(3,4-dihydroxyphosphinyl)-2-oxoethoxy]hydroxyphosphinyl]-2-oxo-3-azetidinyl]carbamic acid, 1,1-dimethylethyl ester, monosodium salt.

(B) (S)-[1-[[2-(3,4-Dihydroxyphosphinyl)-2-oxoethoxy]-hydroxyphosphinyl]-2-oxo-3-azetidinyl]carbamic acid, 1,1-dimethylethyl ester, monosodium salt A solution of the above mixture containing (S)-[1-[[2-[3,4-bis(acetyloxy)phenyl]-2-oxoethoxy]hydroxyphosphinyl]-2-oxo-3-azetidinyl]carbamic acid, 1,1-dimethylethyl ester, monosodium salt in 10 ml of water was treated with 35 equivalents of ammonium acetate (10.0 g, 0.13 mol) and stirred overnight at room temperature. After stirring for 18 hours, the mixture was passed through a 200 ml Dowex (K+ form) ion-exchange column eluting with water and the fractions containing the product were combined and lyophilized to yield 1.6 g of crude material.

(c) (S)-(3-Amino-2-oxo-1-azetidinyl)phosphinic acid, 2-(3,4-dihydroxyphenyl)-2-oxoethyl ester, 1.0 trifluoroacetate salt To a suspension of (S)-[1-[[2-(3,4-dihydroxyphosphinyl)-2-oxoethoxy]hydroxyphosphinyl]-2-oxo-3-azetidinyl]carbamic acid, 1,1-dimethylethyl ester, monosodium salt (750 mg, 1.65 mmol) in 15 ml of dry dichloromethane was added 2 ml of anisole and the mixture was then cooled to −10° C. in an ice-alcohol bath under argon. Trifluoroacetic acid (8 ml) was added and the mixture was stirred. After stirring for 30 minutes at −10° C., the mixture was warmed to 0° C. for 90 minutes. The reaction was diluted with 10 ml of dry toluene and the solvents removed in vacuo at room temperature yielding a yellow oily residue. The residue was triturated with hexanes (3×15 ml) followed by trituration with ether (3×15 ml). The resulting solid was dried in vacuo yielding the title compound.

(D) [2S-[2α,3β(Z)]]-2-[[[1-(2-Amino-4-thiazolyl)-2-[-[2-oxo-1-[[2-(3,4-dihydroxyphenyl)-2-oxoethoxy]hydroxyphosphinyl]-3-azetidinyl]amino]-2-oxoethylidene]amino]oxy]-2-methylpropanoic acid, diphenylmethyl ester, sodium salt (Z)-2-Amino-α-[[2-(diphenylmethoxy)-1,1-dimethyl-2-oxoethyl]imino]-4-thiazoleacetic acid (725 mg, 1.65 mmol) and one equivalent of N-hydroxy-benzotriazole (223 mg, 1.65 mmol) were dissolved in 3 ml of dry dimethylformamide. To this solution was added one equivalent of N,N'-dicyclohexylcarbodiimide at 0° C. under an argon atmosphere. The mixture was stirred for 30 minutes. A separate solution of (S)-(3-amino-2-oxo-1-azetidinyl)phosphinic acid, 2-(3,4-dihydroxyphenyl)-2-oxoethyl ester, 1.0 trifluoroacetate salt (1.65 mmol) in 3 ml of dimethylformamide was treated with three equivalents of diisopropylethylamine (863 μl, 4.95 mmol) and added to the solution of the side chain active ester. The reaction mixture was then stirred for 26 hours at room temperature. The dimethylformamide was removed in vacuo at 25° C. and the resulting residue was partially dissolved in a 10% acetonitrile/water solution (10 ml) and the pH adjusted to pH 6.5 with sodium bicarbonate solution. The aqueous mixture was then passed through a 100 ml Dowex (Na+ form) ion-exchange resin column eluting with 20% acetonitrile/water. The fractions containing the product were combined, the acetonitrile removed in vacuo and the water lyophilized to yield 710 mg of crude material. The crude material was dissolved in 4 ml of water and purified on a 80 ml CHP20P reverse phase column. The column was eluted with a gradient of acetonitrile-water. The product eluted from the column in 30% acetonitrile/water and the fractions containing the product were combined, the acetonitrile removed in vacuo and the water lyophilized to yield 86 mg of the title compound as a colorless solid.

(E) [2S-[2α,3β(Z)]]-2-[[[1-(2-Amino-4-thiazolyl)-2-[-[2-oxo-1-[[2-(3,4-dihydroxyphenyl)-2-oxoethoxy]hydroxyphosphinyl]-3-azetidinyl]amino]-2-oxoethylidene]amino]oxy]-2-methylpropanoic acid, disodium salt To a suspension of [2S-[2α,3β(Z)]]-2-[[[1-(2-amino-4-thiazolyl)-2-[[2-oxo-1-[[2-(3,4-dihydroxyphenyl)-2-oxoethoxy]hydroxyphosphinyl]-3-azetidinyl]amino]-2-oxoethylidene]amino]oxy]-2-methylpropanoic acid, diphenylmethyl ester, sodium salt (85 mg, 0.112 mmol) in 4 ml of dry, distilled dichloromethane was added 0.5 ml of anisole and the mixture cooled to −5° C. in an ice/methanol bath. With stirring and under argon, 1.0 ml of trifluoroacetic acid was added and the mixture was stirred at 0° C. for two hours. Toluene (6 ml) was added and the solvents were removed in vacuo at 20° C. yielding a pale yellow residue. The residue was triturated with hexanes (3×10 ml) followed by trituration with dry ether (2×10 ml) and was then dried in vacuo at room temperature for 30 minutes. The crude salt was dissolved in 4 ml of water and the pH adjusted to pH 6.2 with sodium bicarbonate solution. The aqueous mixture was then chromatographed on a 50 ml CHP20P reverse phase column eluting with water. The fractions containing the desired product were combined and the water lyophilized to yield 38 mg of the title product as a colorless solid.

EXAMPLE 7

[2S-[2α,3β(Z)]]-2-[[[1-(2-Amino-4-thiazolyl)-[-[2-methyl-4-oxo-1-[[2-(3,4-dihydroxyphenyl)oxoethoxy]hydroxyphosphinyl]-3-azetidinyl]amino]-2-oxoethylidene]amino]oxy]-2-methylpropanoic acid, dipotassium salt (A) 2-Chloro-1-[3,4-bis(acetyloxy)phenyl]ethanone A suspension of α-chloro-3',4'-dihydroxyacetophenone (9.33 g, 0.05 mole) in 78 ml of acetic anhydride was treated with 0.1 ml of concentrated sulfuric acid and stirred for 1.5 hours under an argon atmosphere. Initially, the reaction temperature rose to 40° C. and the starting material completely dissolved yielding a clear, colorless solution which was poured onto approximately 300 g of crushed ice. After standing for one hour, the crystallized product was filtered, washed with cold water (200 ml) and dried in vacuo overnight at room temperature; yield: 11.5 g.

(B) 2-Iodo-1-[3,4-bis(acetyloxy)phenyl]ethanone

A solution of 2-chloro-1-[3,4-bis(acetyloxy)phenyl]ethanone (6.77 g, 25 mmol) in 75 ml of dry acetone was refluxed with one equivalent of sodium iodide (3.75 g, 25 mmol) for three hours under an argon atmosphere. The precipitated sodium chloride was filtered and the acetone was removed in vacuo yielding a pale yellow oily residue. Trituration of the residue with 20 ml of 1,1,1-trichloroethane yielded the desired product as a crystalline solid. The solid was filtered and dried in vacuo at room temperature yielding 8.6 g of the title compound as a pale yellow crystalline solid, melting point 168°–170° C.

(C) (2S-trans)-[1-[[2-[3,4-Bis(acetyloxy)phenyl]-2-oxoethoxy]hydroxyphosphinyl]-2-methyl-4-oxo-3-azetidinyl]carbamic acid, 1,1-dimethylethyl ester, monopotassium salt A mixture of (3S-trans)-4-methyl-2-oxo-3-[[(1,1-dimethylethoxy)carbonyl]amino]-1-azetidinyl]phosphonic acid, methyl ester, tetrabutylammonium salt (2.68 g, 5.0 mmol) and two equivalents of 2-iodo-1-[3,4-bis-(acetyloxy)phenyl]ethanone were heated at reflux in 25 ml of 1,1,1-trichloroethane for three hours. The solvent was removed in vacuo and the resulting dark residue was redissolved in 30 ml of acetonitrile and the solvent again removed in vacuo removing any residual trichloroethane. The residue was dissolved in 75 ml of water and the pH adjusted to pH 6.8 with potassium bicarbonate solution. The aqueous mixture was washed with ether (2×75 ml) removing the excess 2-iodo-1-[3,4-bis-(acetyloxy)phenyl]ethanone. Dowex (K+ form) ion-exchange resin (100 ml) was added to the aqueous mixture and stirred overnight. The resin was filtered, washed with additional water and lyophilized yielding crude product as a yellow solid which was purified on a CHP20P reverse phase resin column. The column was eluted with a gradient of acetonitrile-water. The appropriate fractions were combined, concentrated and lyophilized to afford 280 mg of the title compound.

(D) (2S-trans)-[1-[[2-(3,4-Dihydroxyphenyl)-2-oxoethoxy]hydroxyphosphinyl]-2-methyl-4-oxo-3-azetidinyl]carbamic acid, 1,1-dimethylethyl ester, monopotassium salt A solution of (2S-trans)-[1-[[2-[3,4-bis(acetyloxy)-phenyl]-2-oxoethoxy]hydroxyphosphinyl]-2-methyl-4-oxo-3-azetidinyl]carbamic acid, 1,1-dimethylethyl ester, monopotassium salt (166 mg, 0.3 mmol) in 10 ml of water was treated with 150 equivalents of ammonium acetate (3.5 g, 45 mmol) and stirred overnight at room temperature. After stirring for 18 hours, the mixture was passed through a 50 ml Dowex (K+ form) ion exchange column with water, and fractions containing the product were combined and lyophilized to yield 360 mg of crude material. The crude material was purified on a 50 ml CHP20P reverse phase resin column eluting with a gradient of acetonitrile-water. The fractions containing the product were combined, the acetonitrile removed in vacuo and the water lyophilized to yield 118 mg of the title compound as a colorless solid.

(E) (2S-trans)-(3-Amino-2-methyl-4-oxo-1-azetidinyl)-phosphonic acid, 2-(3,4-dihydroxyphenyl)-2-oxoethyl ester, trifluoroacetate salt To a suspension of (2S-trans)-[1-[[2-(3,4-dihydroxyphenyl)-2-oxoethoxy]hydroxyphosphinyl]-2-methyl-4-oxo-3-azetidinyl]carbamic acid, 1,1-dimethylethyl ester, monopotassium salt (117 mg, 0.25 mmol) in 2.5 ml of dry dichloromethane was added 100 μl of anisole and the mixture was then cooled to 0° C. in an ice bath under argon. Trifluoroacetic acid (1 ml) was added and the mixture stirred for two hours. The reaction mixture was diluted with 5 ml of dry toluene and the solvents removed in vacuo at room temperature yielding a yellow oily residue. The residue was triturated with hexanes (2×10 ml) followed by trituration with ether (2×10 ml). The solid was dried in vacuo yielding the title compound.

(F) [2S-[2α,3β(Z)]]-2-[[[1-(2-Amino-4-thiazolyl)[-[2-methyl-4-oxo-1-[[2-(3,4-dihydroxyphenyl)oxoethoxy]hydroxyphosphinyl]-3-azetidinyl]amino]-2-oxoethylidene]amino]oxy]-2-methylpropanoic acid, diphenylmethyl ester, potassium salt (Z)-2-Amino-α-[[2-(diphenylmethoxy)-1,1-dimethyl-2-oxoethoxy]imino]-4-thiazoleacetic acid (117 mg, 0.25 mmol) and one equivalent of N-hydroxybenzotriazole (34 mg, 0.25 mmol) were dissolved in 1.5 ml of dry dimethylformamide and to this solution was added one equivalent of N,N'-dicyclohexylcarbodiimide. The mixture was stirred at room temperature for 30 minutes under an argon atmosphere. A separate solution of (2S-trans)-(3-amino-2-methyl-4-oxo-1-azetidinyl)phosphonic acid, 2-(3,4-dihydroxyphenyl)-2-oxoethyl ester, 1.0 trifluoroacetate salt (0.25 mmol) in 0.75 ml of dimethylformamide was treated with three equivalents of diisopropylethylamine (134 μl, 0.75 mmol) and the mixture was added to the solution of the side chain ester. The reaction mixture was then stirred overnight (18 hours) at room temperature. The dimethylformamide was removed in vacuo at 25° C. and the resulting residue was partially dissolved in a 15% acetonitile/water solution (10 ml) and the pH adjusted to pH 6.5 with potassium bicarbonate solution. Dowex K+ ion-exchange resin (20 ml) was added to the mixture of the crude product and stirred for 30 minutes. The mixture was filtered and the Dowex resin washed with 25 ml of water. The acetonitrile was removed from the filtrate in vacuo and the water lyophilized to yield the crude title compound as a yellow solid. The crude material was dissolved in 3 ml of water and purified on a 30 ml CHP20P reverse phase resin column. The column was eluted with a gradient of acetronitrile-water. The product eluted from the column in 30% acetonitrile/water and the fractions containing the product were combined, the acetonitrile removed in vacuo and the water lyophilized to yield 65 mg of the title compound as a colorless solid.

(G) [2S-[2α,3β(Z)]]-2-[[[1-(2-Amino-4-thiazolyl)[-[2-methyl-4-oxo-1-[[2-(3,4-dihydroxyphenyl)oxoethoxy]hydroxyphosphinyl]-3-azetidinyl]amino]-2-oxoethylidene]amino]oxy]-2-methylpropanoic acid, dipotassium salt To a suspension of [2S-[2α,3β(Z)]]-2-[[[1-(2-amino-4-thiazolyl)-[[2-methyl-4-oxo-1-[[2-(3,4-dihydroxyphenyl)oxoethoxy]hydroxyphosphinyl]-3-azetidinyl]amino]-2-oxoethylidne]amino]oxy]-2-methylpropanoic acid, diphenylmethyl ester, potassium salt (65 mg, 0.082 mmol) in 3 ml of dry distilled dichloromethane, was added 200 μl of anisole and the mixture was cooled to −5° C. in an ice/methanol bath. With stirring and under argon, 500 μl of trifluroacetic acid was added and the mixture was stirred at 0° C. for two hours. Toluene (6 ml) was added and the solvents were removed in vacuo at 20° C. yielding a pale yellow residue. The residue was triturated with hexanes (2×10 ml) followed by trituration with ether (2×10 ml) and dried in vacuo at room temperature for 30 minutes. The crude salt was dissolved in 4 ml of water and the pH adjusted to pH 6.2 with potassium bicarbonate solution. The aqueous mixture was then purified on a 15 ml CHP20P reverse phase resin column in water. The fractions containing the desired product were combined and the water lyophilized to yield 21 mg of the title compound as a colorless solid.

EXAMPLE 8

[2S-[2α,3β(Z)]]-2-[[[1-(2-Amino-4-thiazolyl)-2-[[1-[[2-[[(1,4-dihydro-5-hydroxy-4oxo-2-pyridinyl]carbonyl]amino]ethoxy]hydroxyphosphinyl]-2-methyl-4-oxo-3-azetidinyl]amino]-2-oxoethylidene]amino]oxy]-2-methylpropanoic acid (A) (2S-trans)-1-[Hydroxy[2-[(triphenylmethyl)amino]ethoxy]phosphinyl]-2-methyl-4-oxo-3-azetidinyl]carbamic acid, phenylmethyl ester, monosodium salt A mixture of (2S-trans)-[1-(dihydroxyphosphinyl)-2-methyl-4-oxo-3-azetidinyl]carbamic acid, phenylmethyl ester, 1.0 aniline salt (4.07 g, 10 mmol) and Amberlite (H+ form) ion-exchange resin (30 ml) were combined in 40 ml of 30% acetone/water and stirred for 45 minutes at room temperature.

The mixture was filtered and the resin washed with 20 ml of 30% acetone/water. The acetone was removed in vacuo from the filtrate and the water lyophilized to yield the phosphonic diacid as a yellow solid. The diacid (3.1 g, 10 mmol) was partially dissolved in 60 ml of dry distilled tetrahydrofuran and N-trityl aziridine (2.85 g, 10 mmol) in 20 ml of tetrahydrofuran was added and the resulting mixture was stirred at room temperature, under argon, for 18 hours. The tetrahydrofuran was removed in vacuo and the residue dissolved in 20 ml of acetonitrile/water (1:1). The pH was adjusted to pH 6 with 0.1N sodium hydroxide solution. The solution of the crude material was chromatographed on a column of CHP20P resin eluting with an acetonitrile/water gradient. The desired product eluted from the column in 80% acetonitrile/water. The fractions containing the product were combined, the acetonitrile removed in vacuo and the water lyophilized to yield 1.84 g of the title compound.

(B) (2S-trans)-[1-[(2-Aminoethoxy)hydroxyphosphinyl]-2-methyl-4-oxo-3-azetidinyl]carbamic acid, phenylmethyl ester, trifluoroacetate salt (2S-trans)-[1-[Hydroxy[2-[(triphenylmethyl)amino]ethoxy]phosphinyl]-2-methyl-4-oxo-3-azetidinyl]carbamic acid, monosodium salt (500 mg, 0.8 mmol) was dissolved in 3.5 ml of dry, distilled dichloromethane and 0.8 ml of anisole under an argon atmosphere. The mixture was cooled to 0° C. in an ice bath and, with stirring, 1.6 ml of trifluoroacetic acid was added. The resulting mixture was stirred for three hours between 0° C. and 5° C. The reaction was diluted with 6 ml of dry toluene and the volatiles were removed in vacuo at room temperature. The residue was triturated with hexanes (3×10 ml), anhydrous ether (2×10 ml) and dried in vacuo at room temperature yielding the title compound.

(C) (2S-trans)-[1-[[2-[[[1,4-Dihydro-4-oxo-5-(phenylmethoxy)-2-pyridinyl]carbonyl]amino]ethoxy]hydroxyphosphinyl]-2-methyl-4-oxo-3-azetidinyl]carbamic acid, phenylmethyl ester, monosodium salt To a solution of 1,4-dihydro-4-oxo-5-(phenylmethoxy)-2-pyridinecarboxylic acid (216 mg, 0.88 mmol) and N-hydroxybenzotriazole (119 mg, 0.88 mmol) in 4 ml of dry dimethylformamide was added N,N'-dicyclohexylcarbodiimide (181 mg, 0.88 mmol) and the resulting mixture was stirred at room temperature, under argon, for 45 minutes. A separate solution of (2S-trans)-[1-[(2-aminoethoxy)hydroxyphosphinyl]-2-methyl-4-oxo-3-azetidinyl]carbamic acid, phenylmethyl ester, 1.0 trifluoroacetate salt and diisopropylethylamine (418 μl, 310 mg, 2.4 mmol) in 3 ml of dimethylformamide was added to the dimethylformamide solution containing the active ester and the resulting mixture was stirred overnight (18 hours) at room temperature. The precipitated dicyclohexylurea was removed by filtration and the dimethylformamide was evaporated in vacuo yielding a pale yellow residue. The residue was partially dissolved in 10 ml of acetonitrile/water (1:3) and the pH adjusted to pH 6.8 with sodium bicarbonate solution. The solution was stirred with 11 ml of Dowex (Na+ form) ion-exchange resin. The resin was filtered, washed with 15 ml of 40% acetonitrile/water and the filtrates combined. The acetonitrile was removed in vacuo and the water lyophilized to yield crude (2S-trans)-[1-[[2-[[[1,4-dihydro-4-oxo-5-(phenylmethoxy)-2-pyridinyl]carbonyl]amino]ethoxy]hydroxyphosphinyl]-2-methyl-4-oxo-3-azetidinyl]carbamic acid, phenylmethyl ester, monosodium salt. The material was dissolved in 6 ml of water and purified on a 150 ml CHP20P reverse phase column eluting with a gradient of acetonitrile-water. The appropriate fractions were combined, the acetonitrile was removed in vacuo and the water lyophilized yielding 350 mg of the title compound as a colorless solid.

(D) (2S-trans)-(3-Amino-2-methyl-4-oxo-1-azetidinyl)-phosphonic acid, 2-[[(1,4-dihydro-5-hydroxy-4-oxo-2-pyridinyl)carbonyl]amino]ethyl ester, p-toluenesulfonic acid salt A solution of (2S-trans)-[1-[[2-[[[1,4-dihydro-4-oxo-5-(phenylmethoxy)-2-pyridinyl]carbonyl]amino]ethoxy]hydroxyphosphinyl]-2-methyl-4-oxo-3-azetidinyl]carbamic acid, phenylmethyl ester, monosodium salt (257 mg, 0.424 mmol) and p-toluenesulfonic acid (81 mg, 0.424 mmol) in 3.5 ml of dry dimethylformamide was stirred under a hydrogen atmosphere with 250 mg of 10% palladium on charcoal for two hours at room temperature, affording the title compound which was coupled immediately without isolation or purification.

(E) [2S-[2α,3β(Z)]]-2-[[[1-(2-Amino-4-thiazolyl)-2-[[1-[-[2-[[(1,4-dihydro-5-hydroxy-4-oxo-2-pyridinyl]carbonyl]amino]ethoxy]hydroxyphosphinyl]-2-methyl-4-oxo-3-azetidinyl]amino]-2-oxoethylidene]amino]oxy]-2-methylpropanoic acid, diphenylmethyl ester, sodium salt To the dimethylformamide solution containing (2S-trans)-(3-amino-2-methyl-4-oxo-1-azetidinyl)phosphonic acid, 2-[[(1,4-dihydro-5-hydroxy-4-oxo-2-pyridinyl)carbonyl]amino]ethyl ester, 1.0 p-toluenesulfonic acid salt (0.424 mmol) was added diisopropylethylamine (259 μl, 1.48 mmol) followed by the addition of the N-hydroxybenzotriazole ester of (Z)-2-aminoα-[[2-(diphenylmethoxy)-1,1-dimethyl-2-oxoethoxy]imino]-4-thiazoleacetic acid (354 mg, 0.636 mmol). The mixture was stirred overnight (20 hours) at room temperature under an argon atmosphere. The dimethylformamide mixture was filtered through Celite which was washed with 10 ml of additional dimethylformamide. The dimethylformamide was then removed in vacuo yielding a pale yellow residue which was dissolved in 10 ml of 40% acetonitrile/water (pH 6.8). The aqueous mixture was stirred with 15 ml of Dowex (Na+ form) ion-exchange resin for 30 minutes. The resin was removed by filtration, the acetonitrile evaporated in vacuo and the water lyophilized to yield the crude product. The crude product was dissolved in 10 ml of water and purified on a 150 ml CHP20P reverse phase column. The column was eluted with a gradient of acetonitrile/water. The product eluted from the column in approximately 40% acetonitrile/water. The appropriate fractions were combined, the acetonitrile removed in vacuo and the water lyophilized to yield 190 mg of the title compound as a colorless solid.

(F) [2-S-[2α,3β(Z)]]-2-[[[1-(2-Amino-4-thiazolyl)-2-[[1-[[2-[[(1,4-dihydro-5-hydroxy-4-oxo-2-pyridinyl]carbonyl]amino]ethoxy]hydroxyphosphinyl]-2-methyl-4-oxo-3-azetidinyl]amino]-2-oxoethylidene]amino]oxy]-2-methylpropanoic acid A solution of [2S-[2α,3β(Z)]]-2-[[[1-(2-amino-4-thiazolyl)-2-[[1-[[2-[[(1,4-dihydro-5-hydroxy-4-oxo-2-pyridinyl]carbonyl]amino]ethoxy]hydroxyphosphinyl]-2-methyl-4-oxo-3-azetidinyl]amino]-2-oxoethylidine]amino]oxy]-2-methylpropanoic acid, diphenylmethyl ester, sodium salt (181 mg, 0.225 mmol) in 4 ml of dry, distilled dichloromethane was added 1 ml of anisole and the mixture was cooled to $-5°$ C. in an ice/methanol bath. With stirring and under an argon atmosphere, 5 ml of trifluoroacetic acid was added and the mixture was stirred at $-5°$ C. to $0°$ C. for two hours. Toluene (15 ml) was added and the solvents were removed in vacuo at $20°$ C. yielding a pale yellow oily residue. The residue was triturated with hexane ($3\times6$ ml) followed by trituration with anhydrous ether ($3\times6$ ml) yielding the crude product as a colorless solid. The salt was dissolved in 5 ml of water and the pH adjusted to pH 2.5 with sodium bicarbonate solution. The aqueous mixture was purified on a 75 ml CHP20P reverse phase column, eluting with a gradient of acetonitrile/water. The product eluted from the column in approximately 35% acetonitrile/water. The appropriate fractions were combined, the acetonitrile removed in vacuo and the water lyophilized to yield 122 mg of the title product as a colorless solid.

EXAMPLE 9

[2S-[2α,3β(Z)]]-2-[[[1-(2-Amino-4-thiazolyl)-2-[[1-[[2-[2-[3-(1,4-dihydro-5-hydroxy-4-oxo-2-pyridinyl)-1-oxo-2-propenyl]hydrazino]-2-oxoethoxy]hydroxyphosphinyl]-2-methyl-4-oxo-3-azetidinyl]amino]-2-oxoethylidene]amino]oxy]-2-methylpropanoic acid (A) 1,4-Dihydro-4-oxo-2-[(hydroxy)(methoxy)methyl]-5-(phenylmethoxy)pyridine 1,4-Dihydro-4-oxo-2-(hydroxymethyl)-5-(phenylmethoxy)pyridine (9 g) and activated manganese oxide (26 g) were stirred at room temperature in 100 ml of methanol overnight. After boiling the reaction mixture for 10 minutes, filtering through Hyflo, washing the precipitate with two 50 ml portions of boiling methanol, and evaporating the combined filtrates, the title compound was afforded as beige crystals (9.7 g).

(B) (E)-3-[1,4-Dihydro-4-oxo-5-(phenylmethoxy)-2-pyridinyl]-2-propenoic acid, ethyl ester p-Toluenesulfonic acid (0.5 g), 6.26 g of 1,4-dihydro-4-oxo-2-[(hydroxy)(methoxy)methyl]-5-(phenylmethoxy)pyridine and 8.35 g of (triphenylphosphoranylidene)acetic acid ethyl ester were stirred for three hours at $70°$ C. A clear dark solution was formed. Evaporation of the solvent in vacuo yielded an oily residue of the title compound and triphenylphosphine oxide. This was dissolved in 30 ml of isopropanol. After standing overnight in a refrigerator, the resulting crystals were filtered off, washed with ether and recrystallized from isopropanol (yield: 5.72 g).

(C) (E)-3-[1,4-Dihydro-4-oxo-5-(phenylmethoxy)-2-pyridinyl]-2-propenoic acid (E)-3-[1,4-Dihydro-4-oxo-5-(phenylmethoxy)-2-pyridinyl]-2-propenoic acid, ethyl ester (1.5 g) and 0.29 g of potassium hydroxide were stirred in 30 ml of ethanol for two hours at $50°$ C. After evaporating the solvent, the residue was dissolved in 100 ml of water and filtered. Hydrochloric acid (2N) was added to the filtrate until pH 5 was reached; crystals of the title compound separated. The crystals were filtered and washed with water and dried in vacuo (yield: 1.14 g).

(D) [2S-[2(E),2α,3β]]-[1-[[2-[2-[3-[1,4-Dihydro-4-oxo-5-(phenylmethoxy)-2-pyridinyl]-1-oxo-2-propenyl]hydrazino]-2-oxoethoxy]hydroxyphosphinyl]-2-methyl-4-oxo-3-azetidinyl]carbamic acid, 1,1-dimethylethyl ester, monopotassium salt (E)-3-[1,4-Dihydro-4-oxo-5-(phenylmethoxy)-2-pyridinyl]-2-propenoic acid (393 mg, 1.45 mmol) and N-hydroxybenzotriazole (300 mg, 1.45 mmol) were dissolved at room temperature in dimethylformamide (2.5 ml). The solution was treated with dicyclohexylcarbodiimide and stirred one hour to give the hydroxybenzotriazole ester of (E)-3-[1,4-dihydro-4-oxo-5-(phenylmethoxy)-2-pyridinyl]-2-propenoic acid. This solution was treated with (2S-trans)-[1-[(2-hydrazino-2-oxoethoxy)hydroxyphosphinyl]-2-methyl-4-oxo-2-azetidinyl]carbamic acid, 1,1-dimethylethyl ester, monopotassium salt (507 mg, 1.3 mmol) and stirred at room temperature for 24 hours. The slurry was filtered through Celite and the dimethylformamide evaporated in vacuo. The residue was dissolved in 7 ml of 10% acetonitrile/water (pH 5) and chromatogaphed on a column of CHP20P reverse phase resin eluting with an acetonitrile/water gradient to give the title compound as a white solid (0.440 g), upon evaporation and lyophilization of the appropriate fractions.

(E) [2S-[2α,3β(Z)]]-2-[[[1-(2-Amino-4-thiazolyl)-2-[[1-[[2-[2-[3-(1,4-dihydro-5-hydroxy-4-oxo-2-pyridinyl)-1-oxo-2-propenyl]hydrazino]-2-oxoethoxy]hydroxyphosphinyl]-2-methyl-4-oxo-3-azetidinyl]amino]-2-oxoethylidene]amino]oxy]-2-methylpropanoic acid, diphenylmethyl ester, potassium salt

[2S-[2(E),2α,3β]]-[1-[[2-[2-[3-[1,4-Dihydro-4-oxo-5-(phenylmethoxy)-2-pyridinyl]-1-oxo-2-propenyl]hydrazino]-2-oxoethoxy]hydroxyphosphinyl]-2-methyl-4-oxo-3-azetidinyl]carbamic acid, 1,1-dimethylethyl ester, monopotassium salt (423 mg, 0.66 mmol) was reacted with trifluoroacetic acid (25 ml) and thioanisole (5.2 ml) at room temperature for 13 hours. The solution was treated with toluene (5 ml) and evaporated in vacuo to give a light brown residue. This residue was triturated with hexane ($2\times20$ ml) and ether ($3\times20$ ml) to give a light brown solid which was dried in vacuo for two hours.

(Z)-2-Amino-α-[[2-(diphenylmethoxy)-1,1-dimethyl-2-oxoethoxy]imino]-4-thiazoleacetic acid (308 mg, 0.7 mmol) and hydroxybenzotriazole (95 mg, 0.7 mmol) were dissolved at $-20°$ C. in dimethylformamide (1 ml) and treated with dicyclohexylcarbodiimide (144 mg, 0.7 mmol). The reaction was stirred for 1.5 hours at $0°$ C. To the resulting hydroxybenzotriazole ester was added a dimethylformamide solution (2 ml) of the light brown solid from the above reaction. After two hours at $5°$ C., diisopropylethylamine (450 μl) was added and the reaction was stirred at $5°$ C. for 24 hours.

The solution was filtered through Celite and evaporated free of dimethylformamide. The residue was dissolved in 2 ml of 1:1 acetonitrile/water and applied to a Dowex 50X2 (K+ form) resin column eluting with 20% acetonitrile/water. The appropriate fractions were combined and the solvents were evaporated in vacuo to give a dark red solid. This solid was dissolved in 10% acetone/water at pH 6 and chromatographed on a column of CHP20P reverse phase resin eluting with an acetone/water gradient to yield the title compound (200 mg, 0.23 mmol) was a dark red solid upon evaporation and lyophilization of the appropriate fractions.

(F) [2S-[2α,3β(Z)]]-2-[[[1-(2-Amino-4-thiazolyl)-2-[[1-[[2-[2-[3-(1,4-dihydro-5-hydroxy-4-oxo-2-pyridinyl)-1-oxo-2-propenyl]hydrazino]-2-oxoethoxy]hydroxyphosphinyl]-2-methyl-4-oxo-3-azetidinyl]amino]-2-oxoethylidene]amino]oxy]-2-methyl-propanoic acid A suspension of [2S-[2α,3β(Z)]]-2-[[[1-(2-amino-4-thiazolyl)-2-[[1-[[2-[2-[3-(1,4-dihydro-5-hydroxy-4-oxo-2--pyridinyl)-1-oxo-2-propenyl]hydrazino]-2-oxo-ethoxy]hydroxyphosphinyl]-2-methyl-4-oxo-3-azetidinyl]amino]-2-oxoethylidene]amino]oxy]-2-methyl-propanoic acid, diphenylmethyl ester, potassium salt (200 mg, 0.23 mmol) in dichloromethane (5 ml) at 0° C. was treated sequentially with anisole (0.25 ml) and trifluoroacetic acid (3 ml). This solution was stirred at 0° C. for two hours. Toluene (2 ml) was added and the volatiles were removed (without external heat). The residue was triturated with hexane (5 ml) and ether (2×5 ml) to give a light purple residue. This residue was dissolved in water, the pH adjusted to 2.5, and the solution was chromatographed graphed on a column of CHP20P reverse phase resin eluting with acetone/water. The evaporation and lyophilization of the appropriate fractions gave the title product as a light red solid (12.8 mg).

EXAMPLE 10

[2S-[2α,3β(Z)]]-2-[[[1-(2-Amino-4-thiazolyl)-2-[[1-[[(1,4-dihydro-5-hydroxy-4-oxo-2-pyridinyl)carbonyl]amino]-2-oxo-1-imidazolidinyl]-2-oxoethoxy]hydroxyphosphinyl]-2-methyl-4-oxo-3-azetidinyl]amino]-2-oxoethylidene]amino]oxy]-2-methylpropanoic acid (A) N-[3-(Bromoacetyl)-2-oxo-1-imidazolidinyl]-carbamic acid, 1,1-dimethylethyl ester N-(2-Oxo-1-imidazolidinyl)carbamic acid, 1,1-dimethylethyl ester (12.0 g, 0.06 mmol) was dissolved in dichloromethane (75 ml) containing pyridine (5.2 g, 0.066 mol). The solution was cooled to 0° C. and treated slowly with bromoacetyl bromide (13.3 g, 0.066 mol). The solution was evaporated in vacuo to give a yellow oil. The oil was chromatographed on silica gel (~300 g) eluting with 10% ethyl acetate/dichloromethane. The appropriate fractions were combined and evaporated in vacuo to give the title compound as a white solid, 16.7 g.

(B) N-[3-(iodoacetyl)-2-oxo-1-imidazolidinyl]carbamic acid, 1,1-dimethylethyl ester N-[3-(Bromoacetyl)-2-oxo-1-imidazolidinyl]carbamic acid, 1,1-dimethylethyl ester (20.9 g, 65 mmol) was dissolved in acetone (250 ml) containing sodium iodide (10.5 g, 70 mmol). The solution was stirred at reflux for three hours and filtered hot through Celite. The solution was evaporated in vacuo to give the title compound as a light yellow solid, 23.9 g.

(C) (2S-trans)-[1-[[2-[3-[[(1,1-Dimethylethoxy)-carbonyl]amino]-2-oxo-1-imidazolidinyl]-2-oxo-ethoxy]-hydroxyphosphinyl]-2-methyl-4-oxo-3-azetidinyl]-carbamic acid, phenylmethyl ester, monopotassium salt (3S-trans)-[4-Methyl-2-oxo-3-[[[(phenylmethyl)oxy]-carbonyl]amino]-1-azetidinyl]phosphonic acid, methyl ester, tetrabutylammonium salt (17.1 g, 30 mmol) was placed in 1,1,1-trichloroethane (250 ml) and treated with N-[3-(iodoacetyl)-2-oxo-1-imidazolidinyl]carbamic acid, 1,1-dimethylethyl ester (22.1 g, 60 mmol). The mixture was warmed to reflux and stirred overnight. The solution was evaporated in vacuo to ~150 ml, diluted with 1,1,1-trichloroethane (100 ml), and warmed to reflux for four hours. The solution was evaporated in vacuo to give a dark gum. The gum was dissolved in 10% acetonitrile/water and applied to a column of Dowex 50X2 (K+ form) resin, eluting with water and 10% acetonitrile/water. The appropriate fractions were combined and evaporated in vacuo to ~25 ml (pH 6.1). This solution was applied to a column of CHP20P reverse phase resin and chromatographed, eluting with an acetonitrile/water gradient. The appropriate fractions were combined and evaporated in vacuo to ~100 ml. The solution was lyophilized to give the title compound as a white solid, 12.5 g.

(D) (2S-trans)[1-[[2-(3-Amino-2-oxo-1-imidazolidinyl)-2-oxoethoxy]hydroxyphosphinyl]-2-methyl-4-oxo-3-azetidinyl]carbamic acid, phenylmethyl ester (2S-trans)[1-[[2-[3-[[(1,1-Dimethylethoxy)-carbonyl]amino]-2-oxo-1-imidazolidinyl]-2-oxoethoxy]hydroxyphosphinyl]-2-methyl-4-oxo-3-azetidinyl]carbamic acid, phenylmethyl ester, monopotassium salt (5.9 g, 10 mmol) was treated at 0° C. sequentially with anisole (25 ml) and trifluoroacetic acid (60 ml), and the solution was stirred for six hours. The solution was evaporated in vacuo at ambient temperature and then co-evaporated with toluene (10 ml). The residue was triturated with hexane (50 ml) and diethyl ester (2×50 ml) to give a white solid. The solid was dissolved in water (10 ml) and the pH adjusted to 2.5 with sodium bicarbonate. This solution was chromatographed on a column of CHP20P reverse phase resin and eluted with an acetonitrile/water gradient. The appropriate fractions were combined and evaporated in vacuo to ~100 ml. This was lyophilized to give the title compound as a white solid, 2.520 g.

(E) (2S-trans)-[1-[[2-[3-[[[1,4-dihydro-4-oxo-5-(phenylmethoxy)-2-pyridinyl]carbonyl]amino]-2-oxo-1-imidazolidinyl]-2-oxoethoxy]hydroxyphosphinyl]-2-methyl-4-oxo-3-azetidinyl]carbamic acid, phenylmethoxy ester, monopotassium salt 1,4-Dihydro-4-oxo-5-(phenylmethoxy)-2-pyridinecarboxylic acid (1.19 g, 4.8 mmol) and hydroxybenzotriazole (0.649 g, 4.8 mmol) were stirred in dimethylformamide (12 ml) at room temperature for five minutes. This mixture was treated with dicyclohexylcarbodiimide (1.0 g 4.8 mmol) and stirred for 45 minutes. The mixture was then treated with (2S-trans)[1-[[2-(3-amino-2-oxo-1-imidazolidinyl)-2-oxoethoxy]hydroxyphosphinyl]-2-methyl-4-oxo-3-azetidinyl]carbamic acid, phenylmethyl ester, (2.0 g, 4 mmol) in dimethylformamide (12 ml) and the resulting mixture was stirred at room temperature overnight. The reaction was filtered through Celite and washed with dimethylformamide (20 ml). The combined dimethylformamide filtrates were evaporated to dryness in vacuo. The residue was dissolved in 15% acetonitrile/water (20 ml) and the pH adjusted to 4.0. This solution was applied to a Dowex 50X2 (K+ form) column and eluted with 15% acetonitrile/water. The appropriate fractions were combined and evaporated to ~100 ml in vacuo. The solution was lyophilized to give a white solid. The solid was dissolved in water (15 ml), the pH was adjusted to 5.9 and the solution was chromatographed on a column of CHP20P reverse phase resin. The column was eluted with water and an acetonitrile/water gradient. The appropriate fractions were combined and evaporated to ~150 ml. The solution was lyophilized to give the title compound as an off-white solid, 1.702 g.

(F) [2S-[2α,3β(Z)]]-2-[[[1-(2-Amino-4-thiazolyl)- 2-[[-1-[[2-[3-[[(1,4-dihydro-5-hydroxy-4-oxo-2-pyridinyl)carbonyl]amino]-2-oxo-1-imidazolidinyl]-2-oxoethoxy]hydroxyphosphinyl]-2-methyl-4-oxo-3-azetidinyl]amino]-2-oxoethylidene]amino]oxy]-2-methylpropanoic acid, diphenylmethyl ester, potassium salt (2S-trans)-[1-[[2-[3-[[[1,4-Dihydro-4-oxo-5-(phenylmethoxy)-2-pyridinyl]carbonyl]amino]-2-oxo-1-imidazolidinyl]-2-oxoethoxy]hydroxyphosphinyl]-2-methyl-4-oxo-3-azetidinyl]carbamic acid, phenylmethyl ester, monopotassium salt (850 mg, 1.18 mmol) and p-toluenesulfonic acid (224 mg, 1.18 mmol) were stirred in dimethylformamide (8.5 ml) with 10% palladium on charcoal (550 mg) under a hydrogen atmosphere for one hour and 45 minutes. The reaction was placed under an argon atmosphere and treated with the N-hydroxybenzotriazole ester of (Z)-2-amino-α-[[2-(diphenylmethoxy)-1,1-dimethyl-2-oxoethoxy]imino]-4-thiazoleacetic acid (1.017 g, 1.83 mmol) and N,N-diisopropylethylamine (0.530 g, 4.1 mmol). The solution was stirred for 18 hours at room temperature. The mixture was filtered through Celite and the Celite was washed with dimethylformamide (60 ml). The combined dimethylformamide solutions were evaporated in vacuo. The residue was slurried with Dowex 50X2 (K+ form) (75 ml) in 100 ml of 30% acetonitrile/water for 45 minutes. The Dowex was filtered off, washed with 30% acetonitrile/water (500 ml), and the filtrate evaporated in vacuo to ~200 ml. The solution was lyophilized to give a light brown solid. The solid was dissolved in water (25 ml) and the pH was adjusted to 5.7. This mixture was chromatographed on a CHP20P resin column, eluting with an acetone/water gradient. The appropriate fractions were combined and evaporated to ~120 ml. This solution was lyophilized to give the title compound as a beige solid, 282 mg.

(G) [2S-[2α,3β(Z)]]-2-[[[1-(2-Amino-4-thiazolyl)-2-[[1-[[2-[3-[[(1,4-dihydro-5-hydroxy-4-oxo-2-pyridinyl)carbonyl]amino]-2-oxo-1-imidazolidinyl]-2-oxoethoxy]hydroxyphosphinyl]-2-methyl-4-oxo-3-azetidinyl]amino]-2-oxoethylidene]amino]oxy]-2-methylpropanoic acid

[2S-[2α,3β(Z)]]-2-[[[1-(2-Amino-4-thiazolyl)-2-[[1-[[2-[3-[[(1,4-dihydro-5-hydroxy-4-oxo-2-pyridinyl)carbonyl]amino]-2-oxo-1-imidazolidinyl]-2-oxoethoxy]hydroxyphosphinyl]-2-methyl-4-oxo-3-azetidinyl]amino]-2-oxoethylidene]amino]oxy]-2-methylpropanoic acid, diphenylmethyl ester, potassium salt (270 mg, 0.294 mmol) was slurried in dichloromethane (5 ml) and anisole (1.25 ml) and cooled to 0° C. This mixture was treated with trifluoroacetic acid (6 ml) and stirred at 0° C. for two hours. The mixture was diluted with toluene (3 ml) and evaporated in vacuo. The oily residue was triturated with hexane (2×10 ml) and diethyl ester (2×10 ml) to give a rose solid. The solid was dissolved in water (5 ml) and the pH was adjusted to 2.5 with sodium bicarbonate. This solution was chromatographed on a column of CHP20P reverse phase resin eluting with an acetone/water gradient. The appropriate fractions were combined and evaporated to ~20 ml. This solution was lyophilized to give the title compound as a beige solid, 89 mg.

What is claimed is:

1. A compound having the formula

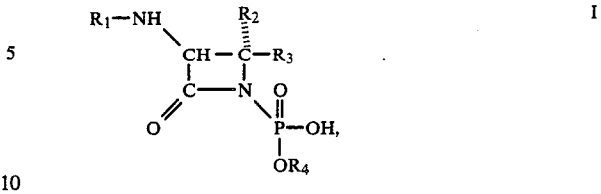

or a pharmaceutically acceptable salt thereof, wherein
$R_1$ is an acyl group derived from a carboxylic acid;
$R_2$ and $R_3$ are the same or different and each is hydrogen, alkyl, alkenyl, alkynyl, cycloalkyl, phenyl, substituted phenyl or a 4, 5, 6 or 7-membered heterocycle or one of $R_2$ and $R_3$ is hydrogen and the other is azido, halomethyl, dihalomethyl, trihalomethyl, alkoxycarbonyl, 2-phenylethenyl, 2-phenylethynyl, carboxyl, $$-CH_2X_1, -S-X_2, -O-X_2, -O-\underset{X_5}{\overset{X_3}{\underset{|}{\overset{|}{C}}}}-X_4,$$

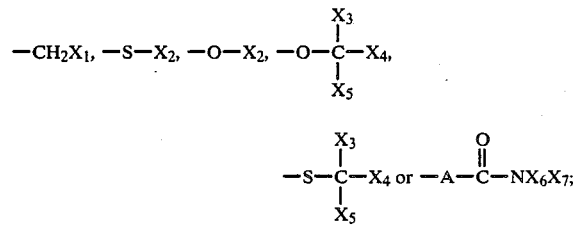

$X_1$ is azido, amino, hydroxy, carboxyl, alkoxycarbonyl, alkanoylamino, phenylcarbonylamino, (substituted phenyl)carbonylamino, alkylsulfonyloxy, phenylsulfonyloxy, (substituted phenyl)sulfonyloxy, phenyl, substituted phenyl, cyano,

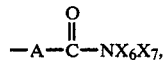

$-S-X_2$, or $-O-X_2$;
$X_2$ is alkyl, substituted alkyl, phenyl, substituted phenyl, phenylalkyl, (substituted phenyl)alkyl, alkanoyl, phenylalkanoyl, (substituted phenyl)alkanoyl, phenylcarbonyl, (substituted phenyl)carbonyl, or heteroarylcarbonyl;
one of $X_3$ and $X_4$ is hydrogen and the other is hydrogen or alkyl, or $X_3$ and $X_4$ when taken together with the carbon atom to which they are attached form a cycloalkyl group;
$X_5$ is formyl, alkanoyl, phenylcarbonyl, (substituted phenyl)carbonyl, phenylalkylcarbonyl, (substituted phenyl)alkylcarbonyl, carboxyl, alkoxycarbonyl, aminocarbonyl, (substituted amino)carbonyl, or cyano;
$X_6$ and $X_7$ are the same or different and each is hydrogen, alkyl, phenyl or substituted phenyl, or $X_6$ is hydrogen and $X_7$ is amino, substituted amino, alkanoylamino or alkoxy, or $X_6$ and $X_7$ when taken together with the nitrogen atom to which they are attached form a 4, 5, 6 or 7-membered heterocycle;
A is $-CH=CH-$, $-(CH_2)_m-$, $-(CH_2)_m-O-$, $-(CH_2)_m-NH-$ or $-CH_2-S-CH_2-$;
m is 0, 1 or 2;
$R_4$ is $-CH_2-Z$,

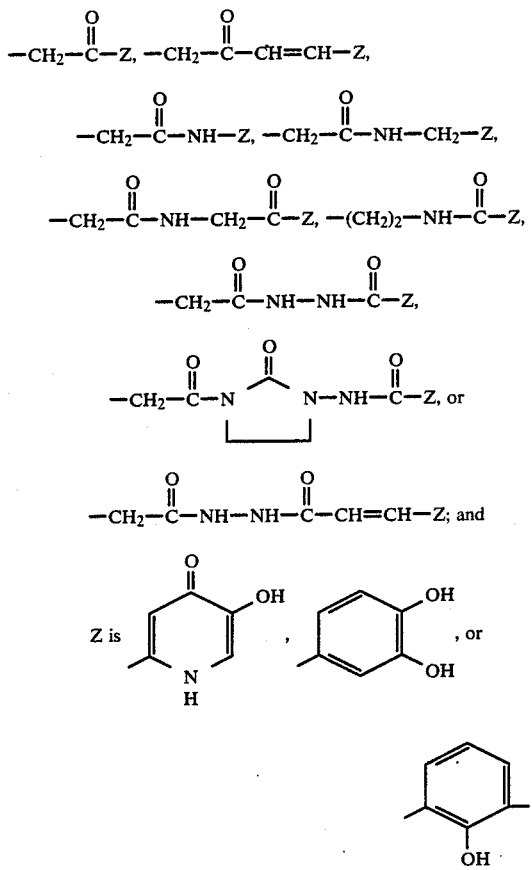

wherein the term "substituted alkyl" refers to alkyl groups substituted with azido, amino, halogen, hydroxy, carboxy, cyano, alkoxycarbonyl, aminocarbonyl, alkanoyloxy, alkoxy, phenyloxy, (substituted phenyl)oxy, mercapto, alkylthio, phenylthio, (substituted phenyl)thio, alkylsulfinyl or alkylsulfonyl groups;

the term "substituted phenyl" refers to a phenyl group substituted with 1, 2 or 3 amino, halogen, hydroxyl, trifluoromethyl, alkyl of 1 to 4 carbon atoms, alkoxy of 1 to 4 carbon atoms, alkanoyloxy, aminocarbonyl, or carboxy groups;

the term "substituted amino" refers to a group having the formula $-NX_8X_9$ wherein $X_8$ is hydrogen, alkyl, phenyl, substituted phenyl, phenylalkyl or (substituted phenyl)alkyl, and $X_9$ is alkyl, phenyl, substituted phenyl, phenylalkyl, (substituted phenyl)alkyl, hydroxy, cyano, alkoxy, phenylalkoxy or amino;

the term "heteroaryl" refers to pyridinyl, furanyl, pyrrolyl, thienyl, 1,2,3-triazolyl, 1,2,4-triazolyl, imidazolyl, thiazolyl, thiadiazolyl, pyrimidinyl, oxazolyl, triazinyl, tetrazolyl or one of the above groups substituted with one or more halogen, hydroxy, nitro, amino, cyano, trifluoromethyl, alkyl of 1 to 4 carbon atoms, alkoxy of 1 to 4 carbon atoms, alkylsulfonyl, phenyl, substituted phenyl, 2-furfurylideneamino, benzylideneamino, or substituted alkyl wherein the alkyl group has 1 to 4 carbon atoms, groups;

the term "a 4,5,6 or 7-membered heterocycle" refers to pyridinyl, furanyl, pyrrolyl, thienyl, 1,2,3-triazolyl, 1,2,4-triazolyl, imidazolyl, thiazolyl, thiadiazolyl, pyrimidinyl, oxazolyl, triazinyl, tetrazolyl, azetidinyl, oxetanyl, thietanyl, piperidinyl, piperazinyl, imidazolylidinyl, oxazolidinyl, pyrrolidinyl, tetrahydropyrimidinyl, dihydrothiazolyl or hexahydroazepinyl or one of the above groups substituted with one or more oxo, halogen, hydroxy, nitro, amino, cyano, trifluoromethyl, alkyl of 1 to 4 carbon atoms, alkoxy of 1 to 4 carbon atoms, alkylsulfonyl, phenyl, substituted phenyl, 2-furfurylideneamino, benzylideneamino, or substituted alkyl wherein the alkyl group has 1 to 4 carbon atom, groups.

2. A compound in accordance with claim 1 wherein $R_4$ is $-CH_2-Z$.

3. A compound in accordance with claim 1 wherein $R_4$ is

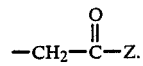

4. A compound in accordance with claim 1 wherein $R_4$ is

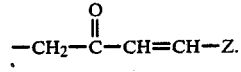

5. A compound in accordance with claim 1 wherein $R_4$ is

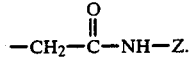

6. A compound in accordance with claim 1 wherein $R_4$ is

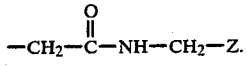

7. A compound in accordance with claim 1 wherein $R_4$ is

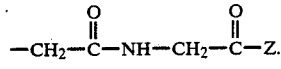

8. A compound in accordance with claim 1 wherein $R_4$ is

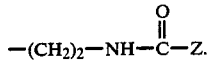

9. A compound in accordance with claim 1 wherein $R_4$ is

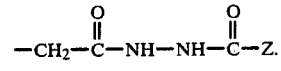

10. A compound in accordance with claim 1 wherein $R_4$ is

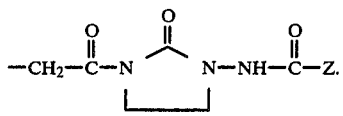

11. A compound in accordance with claim 1 wherein $R_4$ is

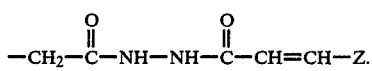

12. A compound in accordance with claim 1 wherein $R_2$ and $R_3$ are the same or different and each is hydrogen or alkyl.

13. A compound in accordance with claim 1 wherein $R_1$ is

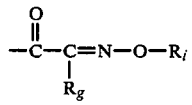

wherein $R_g$ is 2-amino-4-thiazolyl and $R_i$ is methyl, ethyl, carboxymethyl, 1-carboxy-1-methylethyl, 1-carboxy-1-ethyl or

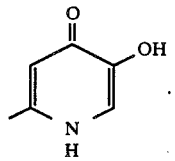

wherein s is 1, 2 or 3.

14. A compound in accordance with claim 1 wherein Z is

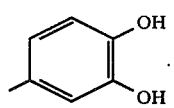

15. A compound in accordance with claim 1 wherein Z is

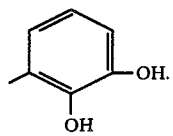

16. A compound in accordance with claim 1 wherein Z is

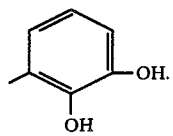

* * * * *